United States Patent
Fan et al.

(10) Patent No.: US 9,151,713 B2
(45) Date of Patent: Oct. 6, 2015

(54) SENSITIVE INTRACAVITY BIOSENSING PLATFORM AND METHODS FOR DETECTION THEREWITH

(75) Inventors: Xudong Fan, Saline, MI (US); Yuze Sun, Rockville, MD (US); Wonsuk Lee, Ann Arbor, MI (US)

(73) Assignee: The Regents Of The University Of Michigan, Ann Arbor, MI (US)

(*) Notice: Subject to any disclaimer, the term of this patent is extended or adjusted under 35 U.S.C. 154(b) by 92 days.

(21) Appl. No.: 13/979,099

(22) PCT Filed: Jan. 10, 2012

(86) PCT No.: PCT/US2012/020774
§ 371 (c)(1),
(2), (4) Date: Jul. 10, 2013

(87) PCT Pub. No.: WO2012/096955
PCT Pub. Date: Jul. 19, 2012

(65) Prior Publication Data
US 2014/0017700 A1 Jan. 16, 2014

Related U.S. Application Data

(60) Provisional application No. 61/431,182, filed on Jan. 10, 2011.

(51) Int. Cl.
G01N 21/64 (2006.01)
G01N 33/58 (2006.01)

(52) U.S. Cl.
CPC .......... *G01N 21/6428* (2013.01); *G01N 21/645* (2013.01); *G01N 33/582* (2013.01); *G01N 21/6402* (2013.01); *G01N 2021/6441* (2013.01); *G01N 2021/6484* (2013.01)

(58) Field of Classification Search
None
See application file for complete search history.

(56) References Cited

U.S. PATENT DOCUMENTS

| 7,693,369 B2 | 4/2010 | Fan et al. |
| 2010/0163748 A1 | 7/2010 | Dhadwal |

FOREIGN PATENT DOCUMENTS

WO    WO-2009025898 A2 *    2/2009

OTHER PUBLICATIONS

Biosensors & Bioelectronics 24 (3), 461 (May 9, 2008).*
Zhu, Hongying, et al., "A universal label-free biosensing platform based on opto-fluidic ring resonators." Frontiers in Pathogen Detection, 2009, Proc. of SPIE vol. 7167, pp. 71670I-1-71670I-13 (in English).
Suter, Jonathan D., et al., "Label-free DNA methylation analysis using the optofluidic ring resonator sensor." 2009, Proc. of SPIE vol. 7322, pp. 732208-1-732208-8 (in English).
W. Lee and X. Fan, "Rapid DNA Detection via Optofluidic Lasers using Saturation Dye," in *Conference on Lasers and Electro-Optics* 2012, OSA Technical Digest (online) (Optical Society of America, 2012), paper CTu1L.4.
International Search Report and Written Opinion of the International Searching Authority for PCT/US2012/020774, (in English) mailed May 25, 2012; ISA/KR.
M. Hossein-Zadeh, and K. J. Vahala, "Fiber-taper coupling to Whispering-Gallery modes of fluidic resonators embedded in a liquid medium," Opt. Express 14, 10800-10810 (2006).
M. Sumetsky, "Optical fiber microcoil resonator," Opt. Express, 10 (2004).
N. M. Hanumegowda, C. J. Stica, B. C. Patel, I. M. White, and X. Fan, "Refractometric sensors based on microsphere resonators," Appl. Phys. Lett. 87, 201107 (2005).
V. S. Ilchenko, X. S. Yao, and L. Maleki, "Pigtailing the high-Q microsphere cavity: a simple fiber coupler for optical whispering-gallery modes," Opt. Lett. 24, 723-725 (1999).
M. Berggren, A. Dodabalapur, R. E. Slusher, and Z. Bao, "Light amplification in organic thin films using cascade energy transfer," Nature 389, 466-469 (1997).
T. Forster, "Transfer mechanisms of electronic excitation," Disc. Faraday Soc. 27, 7-17 (1959).
R. L. Armstrong, J. G. Xie, T. E. Ruekgauer, and R. G. Pinnick, "Energy-transfer-assisted lasing from microdroplets seeded with fluorescent sol," Opt. Lett. 17, 943-945 (1992).
A. Rose, Z. Zhu, C. F. Madigan, T. M. Swager, and V. Bulovic, "Sensitivity gains in chemosensing by lasing action in organic polymers," Nature 434, 876-879 (2005).
A. W. Wun, P. T. Snee, Y. Chan, M. G. Bawendi, and D. G. Nocera, "Non-linear transduction strategies for chemo/biosensing on small length scales," J. Mater. Chem. 15, 2697-2706 (2005).
H. Moon, Y.-T. Chough, and K. An, "Cylindrical Microcavity Laser Based on the Evanescent-Wave-Coupled Gain," Phys. Rev. Lett. 85, 3161-3164 (2000).
I. M. White, H. Oveys, and X. Fan, "Liquid Core Optical Ring Resonator Sensors," Opt. Lett. 31, 1319-1321 (2006).
V. Zamora, A. Díez, M. V. Andrés, and B. Gimeno, "Refractometric sensor based on whisperinggallery modes of thin capillaries," Opt. Express 15, 12011-12016 (2007).
M. Sumetsky, R. S. Windeler, Y. Dulashko, and X. Fan, "Optical liquid ring resonator sensor," Opt. Express 15, 14376-14381 (2007).

(Continued)

*Primary Examiner* — James Martinell
(74) *Attorney, Agent, or Firm* — Harness, Dickey & Pierce, P.L.C.

(57) ABSTRACT

The present disclosure provides a method of detecting a target analyte, by binding the target analyte and a probe with at least one fluorophore to form a fluid composition. The fluid composition is excited within a laser cavity. The method comprises measuring a laser emission from the fluid composition based on an interaction between the target analyte and the probe. In certain aspects, the method provides hybridizing the target analyte and the probe, prior to the exciting. In certain variations, the methods comprise detecting a target analyte by measuring a laser emission from the fluid composition based on an interaction between the target analyte, where the interaction is probe energy transfer, intercalation, hybridization of the target analyte and the probe, or combinations thereof. The energy transfer can include fluorescence resonance energy transfer (FRET), FRET with a molecular-beacon, or cavity-assisted radiative energy transfer, by way of non-limiting example.

20 Claims, 18 Drawing Sheets

(56) References Cited

OTHER PUBLICATIONS

X. Fan, I. M. White, H. Zhu, J. D. Suter, and H. Oveys, "Overview of novel integrated optical ng resonator bio/chemical sensors," in Laser Resonators and Beam Control IX, A. V. Kudryashov, A. H. Paxton, and V. S. Ilchenko, eds. (San Jose, 2007), p. 6452M.

H. Zhu, I. M. White, J. D. Suter, P. S. Dale, and X. Fan, "Analysis of biomolecule detection with optofluidic ring resonator sensors," Opt. Express 15, 9139-9146 (2007).

N. A. Mortensen, S. Xiao, and J. Pedersen, "Liquid-infiltrated photonic crystals: light-matter interactions for lab-on-a-chip applications," Microfluid. Nanofluid. 4: 117 (2008).

S. Arnold, and L. M. Folan, "Energy transfer and the photon lifetime within an aerosol particle," Opt. Lett. 14, 387-389 (1989).

P. T. Leung, and K. Young, "Theory of enhanced energy transfer in an aerosol particle," J. Chem. Phys. 89, 2894-2899 (1988).

S. Gotzinger, L. de S. Menezes, A. Mazzei, S. Kuhn, V. Sandoghdar, and O. Benson, "Controlled photon transfer between two individual nanoemitters via shared high-Q modes of a microsphere resonator," Nano Lett. 6, 1151-1154 (2006).

C. F. Bohren, and D. R. Huffman, Absorption and Scattering of Light by Small Particles (John Wiley & Sons, New York, 1998). pp. vii-xiv only.

* cited by examiner

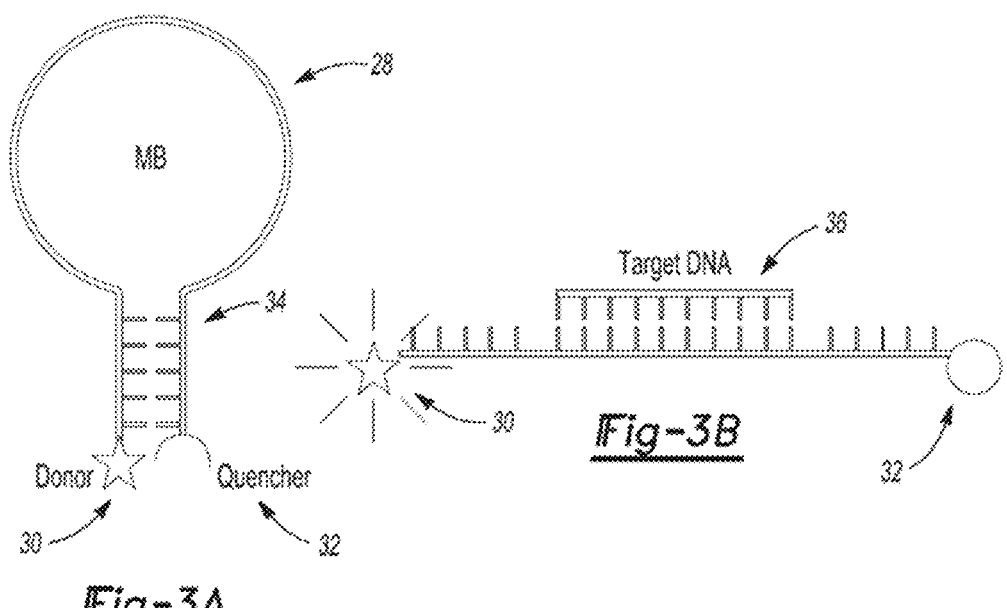
*Fig-3A*
*Fig-3B*
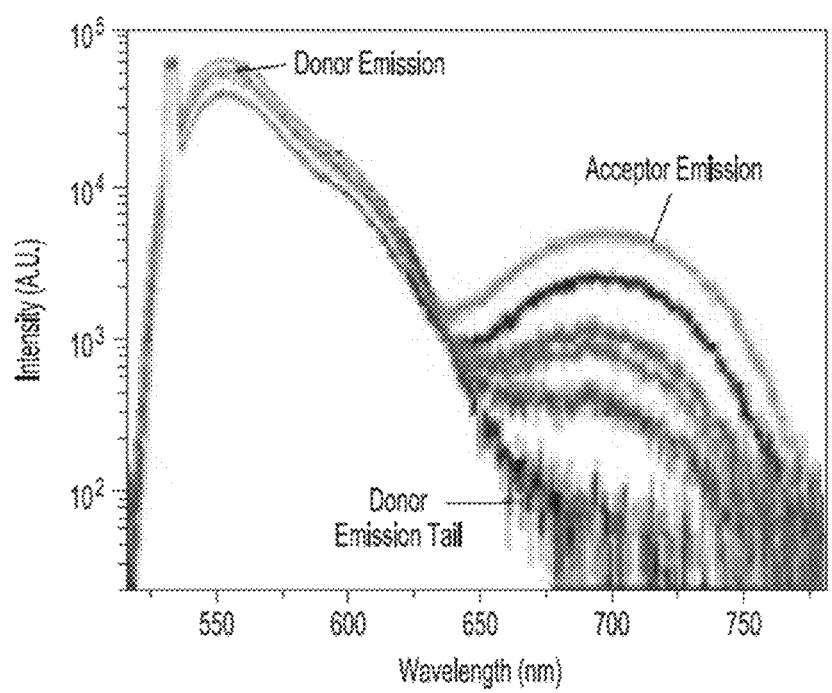
*Fig-4*

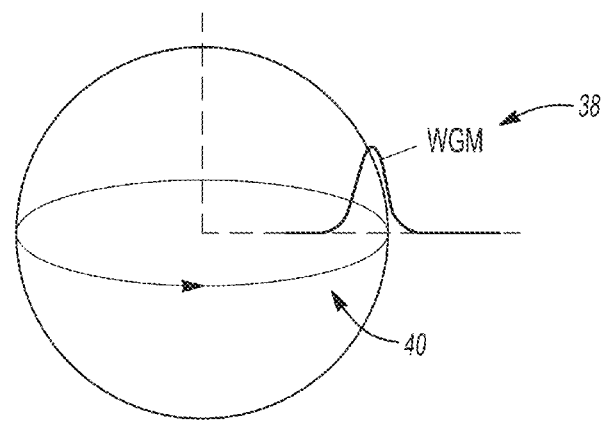
*Fig-5*
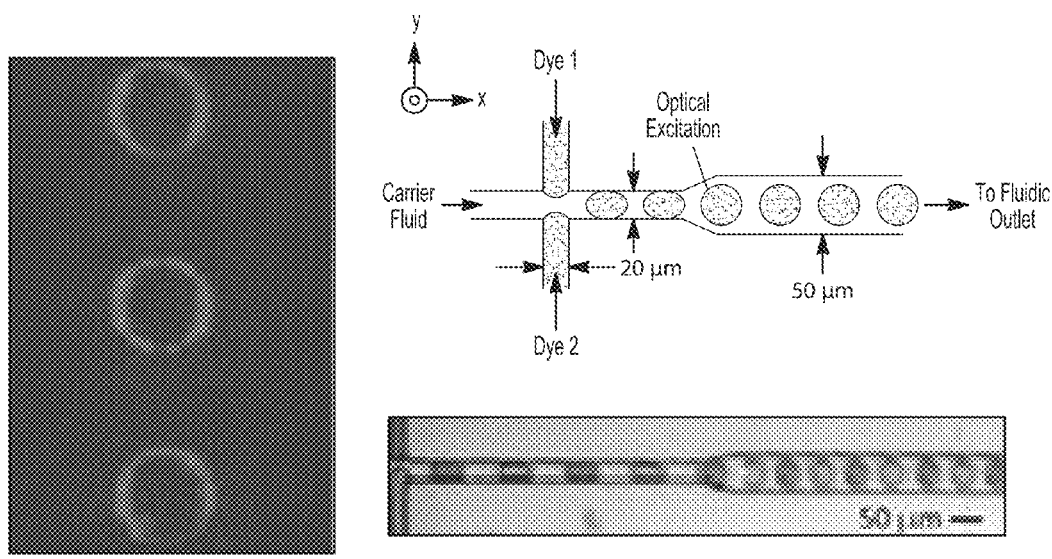
*Fig-6A*   *Fig-6B*

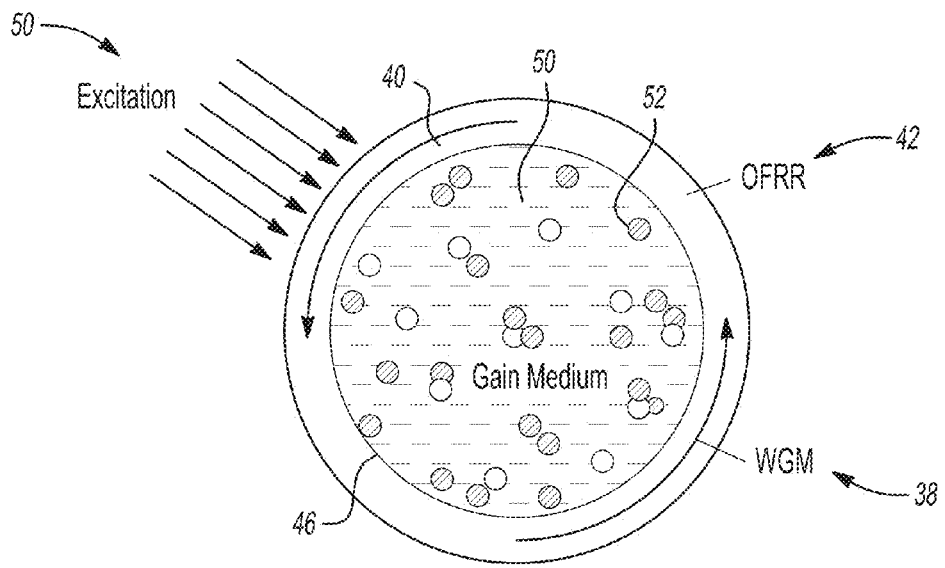
Fig-8
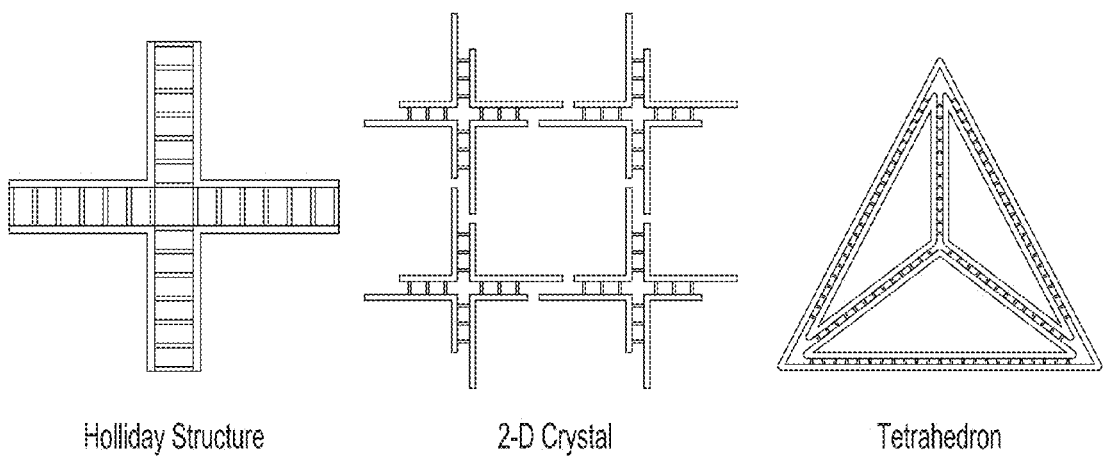
Holliday Structure  
Fig-9A
2-D Crystal  
Fig-9B
Tetrahedron  
Fig-9C

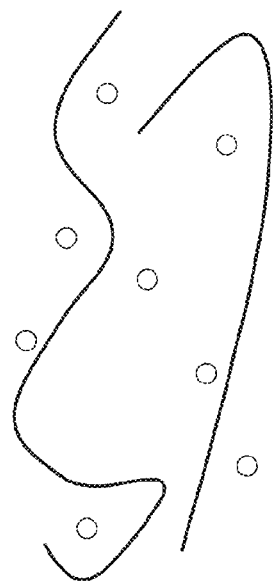
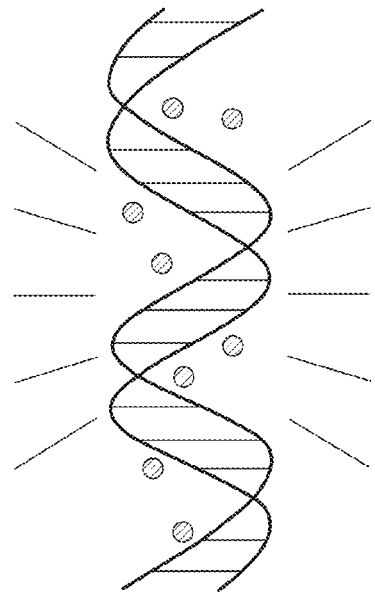
Fig-23A    Fig-23B
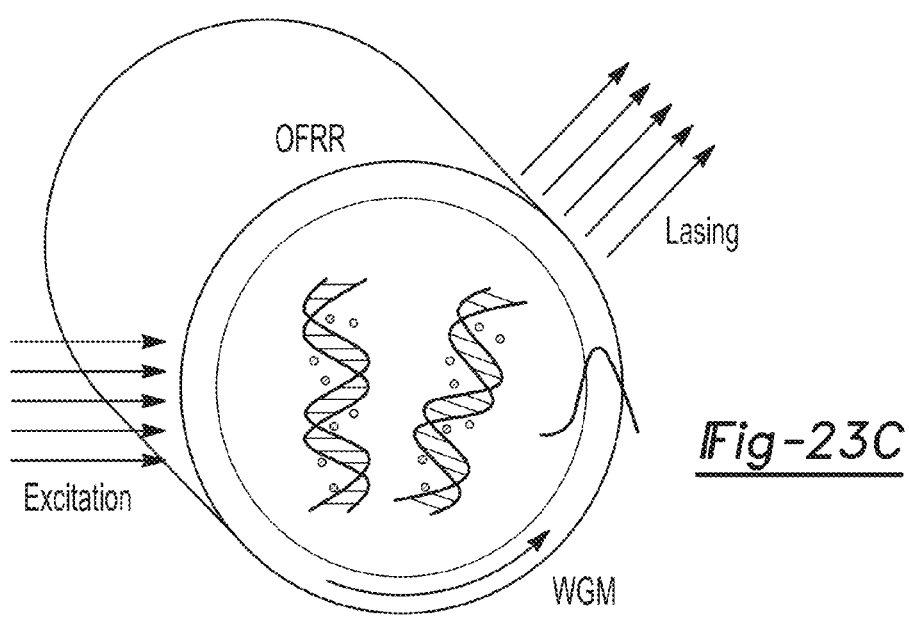
Fig-23C

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 1
acaacaaaga caatacatag g                                             21

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
tgttgtttct gttatgtatc c                                             21

<210> SEQ ID NO 3
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 3
tgttgtttct attatgtatc c                                             21
```

SENSITIVE INTRACAVITY BIOSENSING PLATFORM AND METHODS FOR DETECTION THEREWITH

CROSS-REFERENCE TO RELATED APPLICATIONS

This application is a National Stage of International Application No. PCT/US2012/020774 filed on Jan. 10, 2012, which claims the benefit of U.S. Provisional Application No. 61/431,182, filed on Jan. 10, 2011. The entire disclosures of each of the above applications are incorporated herein by reference.

GOVERNMENT RIGHTS

This invention was made with U.S. Government support under CBET1037097 awarded by National Science Foundation. The Government has certain rights in the invention.

REFERENCE TO A SEQUENCE LISTING

The material in the ASCII text file entitled "2115_004778_SeqList" is hereby incorporated by reference in its entirety. The ASCII text files entitled entitled "2115_004778_SeqList" was created on Aug. 16, 2013 and the size is 856 bytes.

FIELD

The present disclosure relates to methods of detecting and an apparatus for detecting biological target analytes by employing colorimetric detection, such as optofluidic microlasers.

BACKGROUND

This section provides background information related to the present technology which is not necessarily prior art.

Rapid, cost-effective, specific, and high-throughput detection of DNA sequences is a topic of major scientific interest. For example, its application areas include clinical diagnosis of genetic and pathogenic diseases, single nucleotide polymorphism genotyping, drug discovery, environmental studies, homeland security, and forensic analysis. Numerous analytical techniques, such as electrochemical sensors, capillary electrophoresis, optical sensors, mechanical sensors, have been developed to detect DNA, including fluorescence based detection.

Considerable efforts have been made to develop DNA detectors and analyzers, particularly for example, single-nucleotide polymorphisms (SNPs) that differentiate the target single-stranded DNA (ssDNA) from those with a single-base mismatch owing to the key role of DNA in the transfer of genetic information. Many technological advances have been made to provide tools to analyze SNPs. Most of those technologies utilize fluorescence from the dye labeled on a DNA probe, which adds costs and detection processes. In comparison, high resolution melt (HRM) analysis is a unique technology that relies on intercalating saturation dyes to monitor double-stranded DNA (dsDNA). Saturation dye has a very high fluorescence quantum yield in the presence of dsDNA, but its quantum yield diminishes when the dsDNA becomes ssDNA at relatively high temperature. HRM uses the saturation dye directly and does not require any costly labeling processes. HRM has to scan the temperature to differentiate SNPs, which slows detection. Additionally, the fluorescence difference between the target DNA and single-based mismatched DNA is small. It would be desirable to have a method, system and apparatus for rapid detection of target DNA or other target analytes.

SUMMARY

In various aspects, the present disclosure provides a method of detecting a target analyte, by binding the target analyte and a probe with at least one fluorophore to form a fluid composition. The method also comprises exciting a fluid composition within a laser cavity and measuring a laser emission from the fluid composition based on an interaction between the target analyte and the probe. In yet other aspects, the method provides hybridizing the target analyte and the probe, prior to the exciting.

In certain aspects, other methods of detecting a target analyte may include exciting a fluid composition within a laser cavity. The fluid composition comprises a target analyte labeled with an acceptor chromophore, such as an acceptor fluorophore, and a probe labeled with a donor chromophore, such as a donor fluorophore. An emission from at least one of the acceptor fluorophore or the donor fluorophore is measured by exciting the fluid composition. Thus, the target analyte can be detected based on the measured emissions from the acceptor fluorophore and/or the donor fluorophore, indicating an energy transfer between the acceptor fluorophore and the donor fluorophore. In certain variations, the method further comprises hybridizing the target analyte labeled with the acceptor fluorophore and the labeled with the donor fluorophore to form the fluid composition, prior to exciting the fluid composition.

In yet other aspects, the present disclosure provides an optical biosensing apparatus for detecting a target analyte that comprises: an optofluidic ring resonator (OFRR). The optofluidic ring resonator comprises a thin-walled fused silica microcapillary comprising a volume of the target analyte; and a laser cavity, wherein the target analyte is detected within the laser cavity based on a fluorescence of the target analyte.

In yet other aspects, the present disclosure provides a method of detecting a target, such as a nucleic acid like a DNA molecule. The method may comprise: labeling the DNA molecule with an acceptor fluorophore and labeling at least one probe with a donor fluorophore. After labeling the hybridized DNA molecule and the hybridized probe are mixed to create a fluid composition, wherein upon hybridization the acceptor fluorophore and the donor fluorophore are separated by about 10 to about 30 base pairs. The method also comprises exciting the fluid composition within a laser cavity, measuring the acceptor fluorophore emission and the donor fluorophore emission with in the fluid composition and detecting the target analyte based an energy transfer between the acceptor fluorophore and the donor fluorophore, wherein the energy transfer is fluorescence resonance energy transfer (FRET).

In yet other aspects, the present disclosure provides a method of detecting a DNA molecule, the method comprising combining a single-stranded DNA molecule and a single-stranded probe with a saturation dye to form a fluid composition, exciting the fluid composition within a laser cavity and measuring a laser emission from the fluid composition based on an interaction between the single-stranded DNA and the single-stranded probe.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2A depicts a donor and acceptor labeled on a probe and target DNA; and FIG. 2B depicts a variation of the labeling method;

FIGS. 3A-3B illustrate DNA detection based on a molecular beacon in accordance with the present disclosure; FIG. 3A depicts the molecular beacon in the absence of the target DNA; and FIG. 3B depicts the molecular beacon in the presence of the target DNA;

FIG. 4 illustrates a FRET signal with a decreased donor emission and an increased acceptor emission;

FIG. 5 illustrates a whispering gallery mode (WGM) forms due to total internal reflection of the light at the curved boundary in accordance with certain aspects of the present disclosure;

Figure 6C:
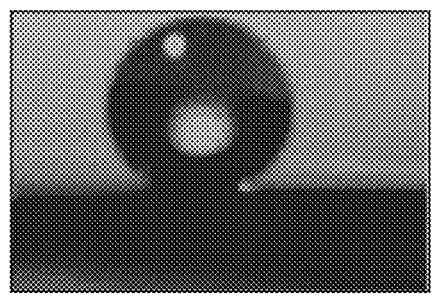
Figure 6D:
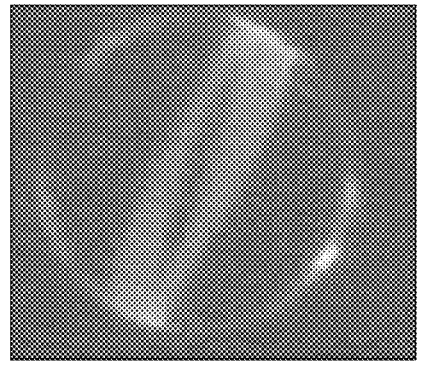
Figure 6E:
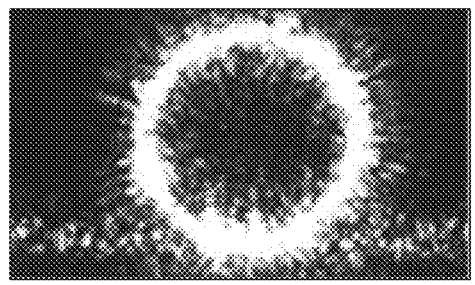
Figure 6F:
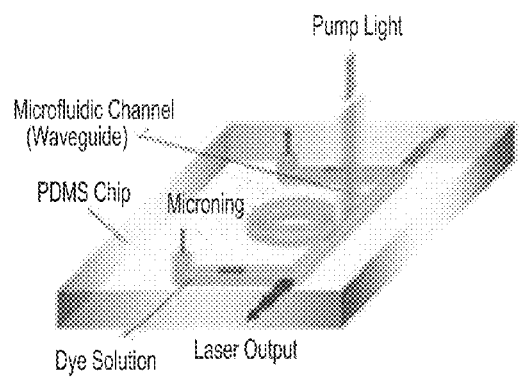
Figure 6G:
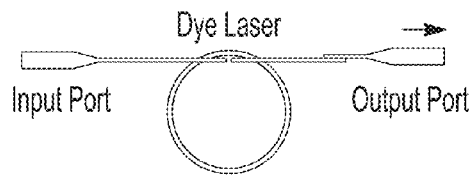
Figure 6G:
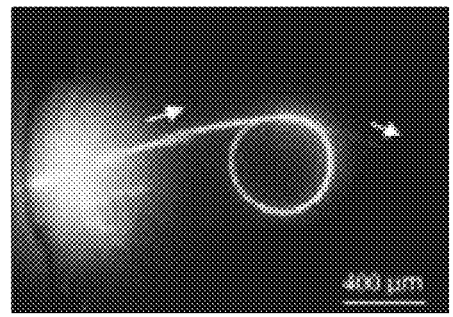
Figure 6H:
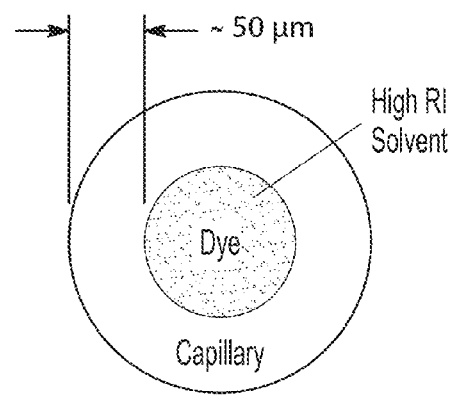
Figure 7A:
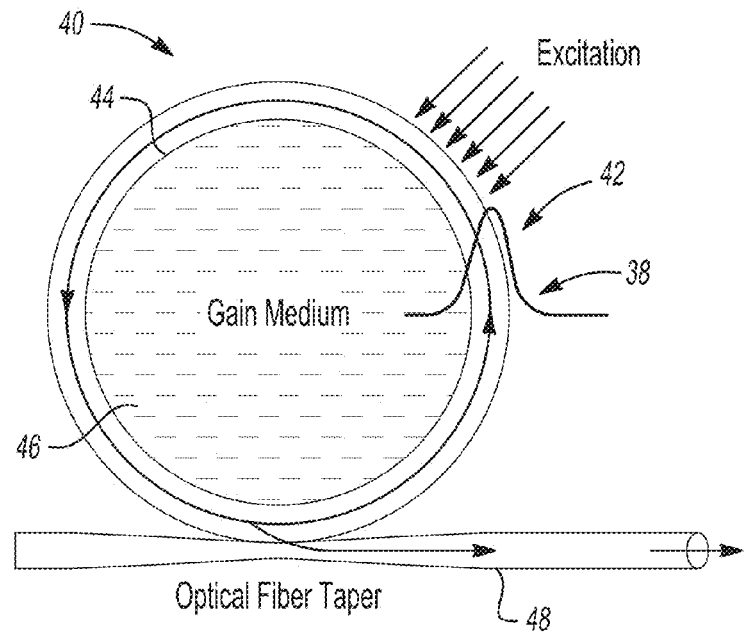
Figure 7B:
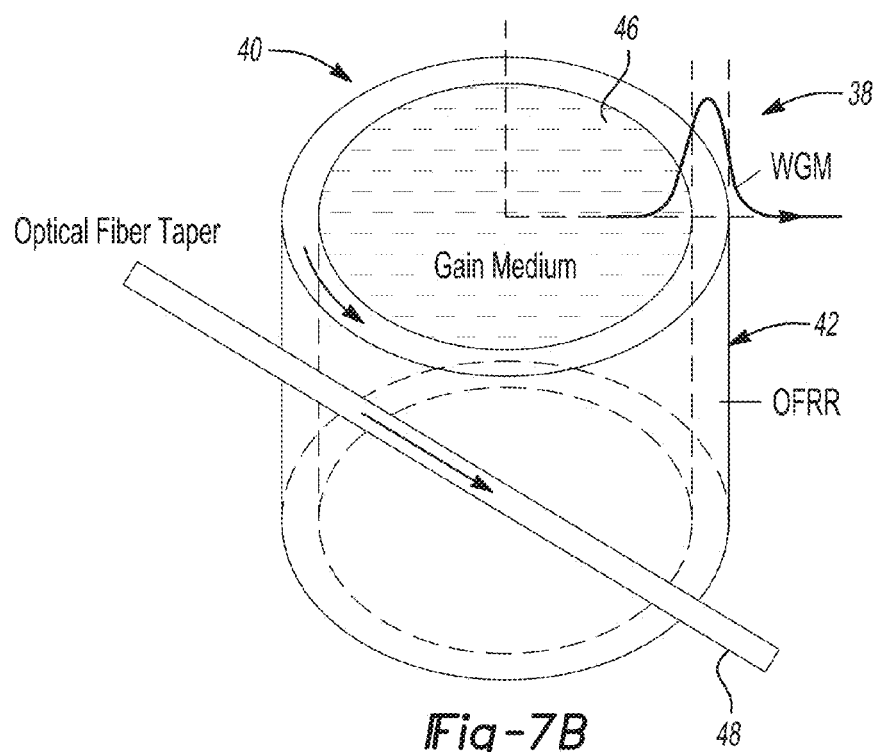
Figure 10A:
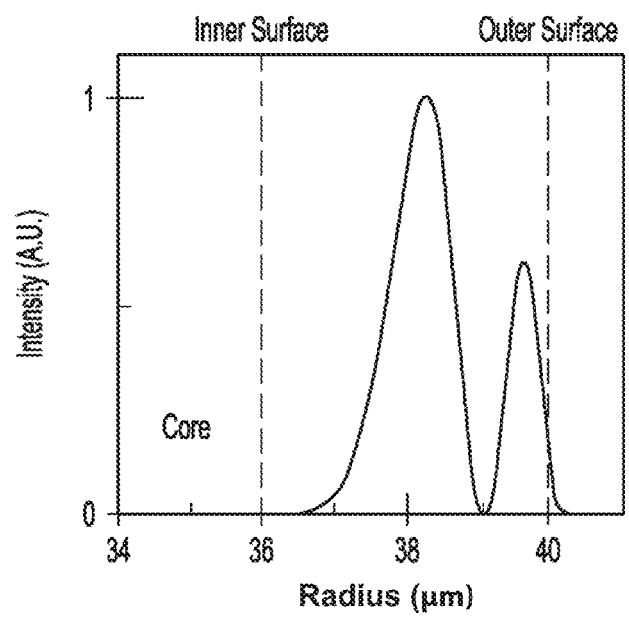
Figure 10B:
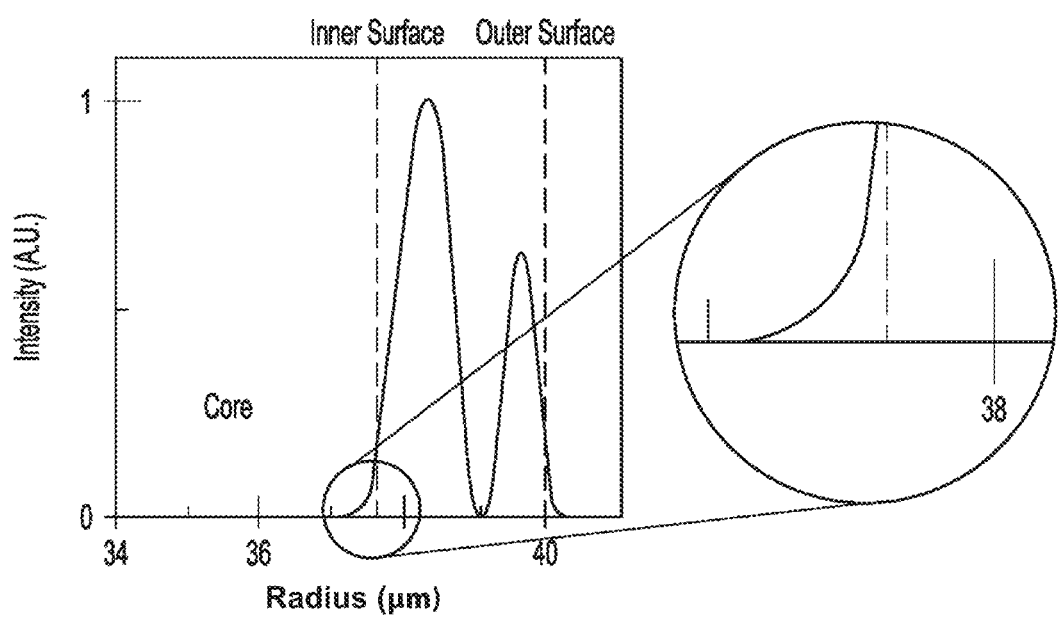
Figure 11A:
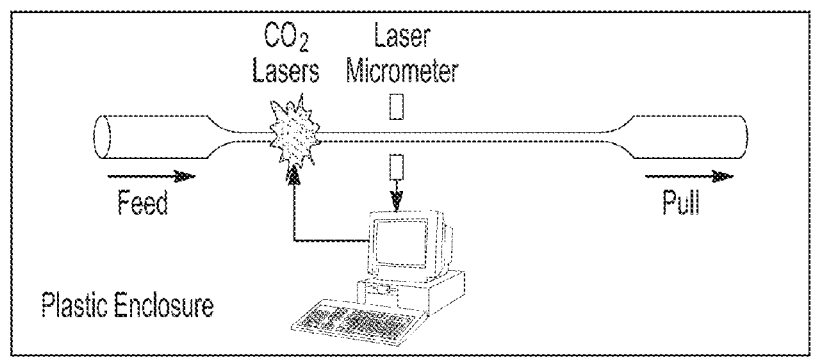
Figure 11B:
Figure 11C:
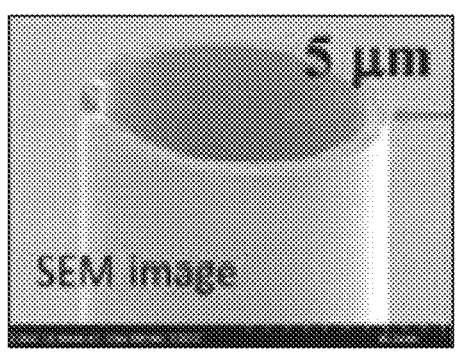
Figure 11D:
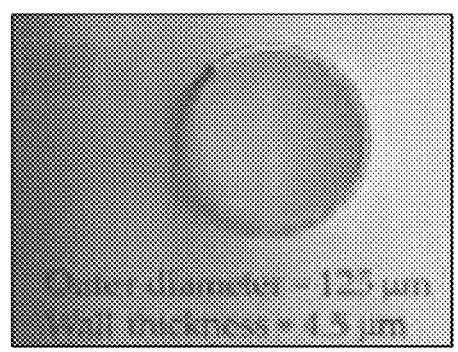
Figure 12A:
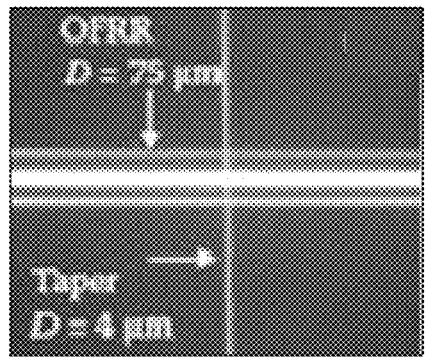
Figure 12B:
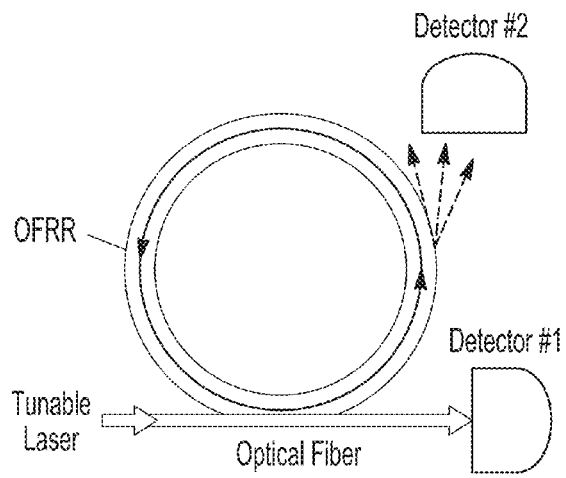
Figure 12C:
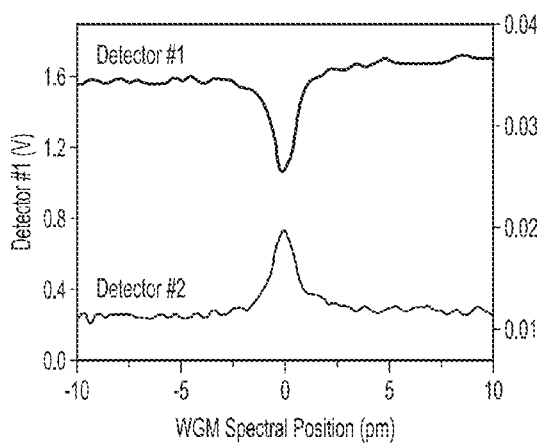
Figure 12D:
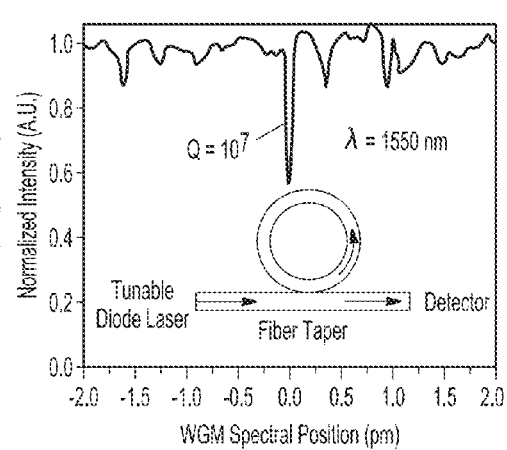
Figure 13A:
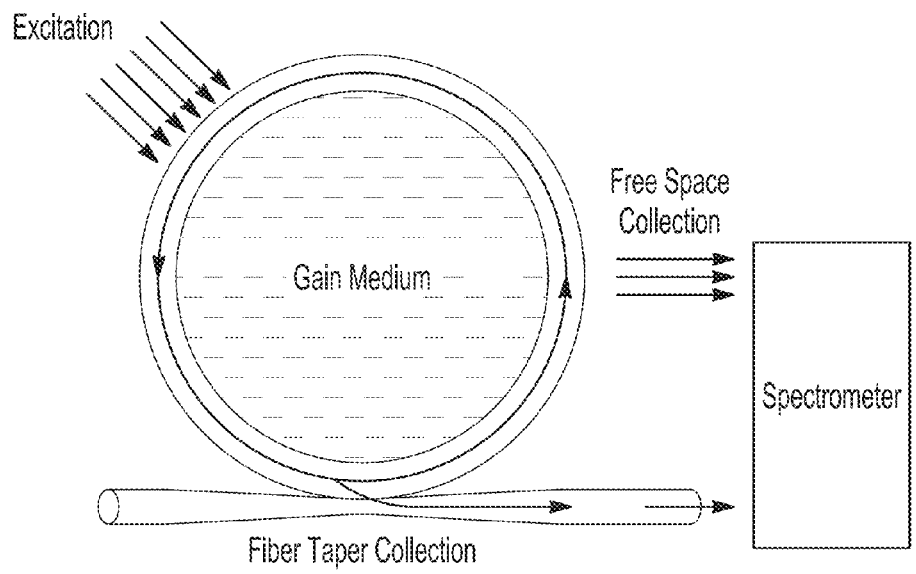
Figure 13B:
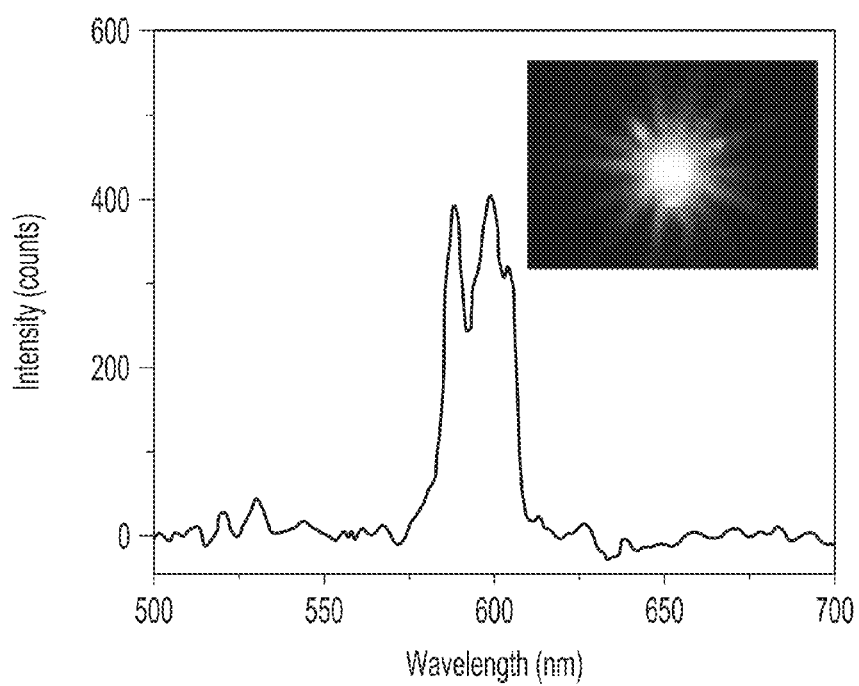
Figure 13C:
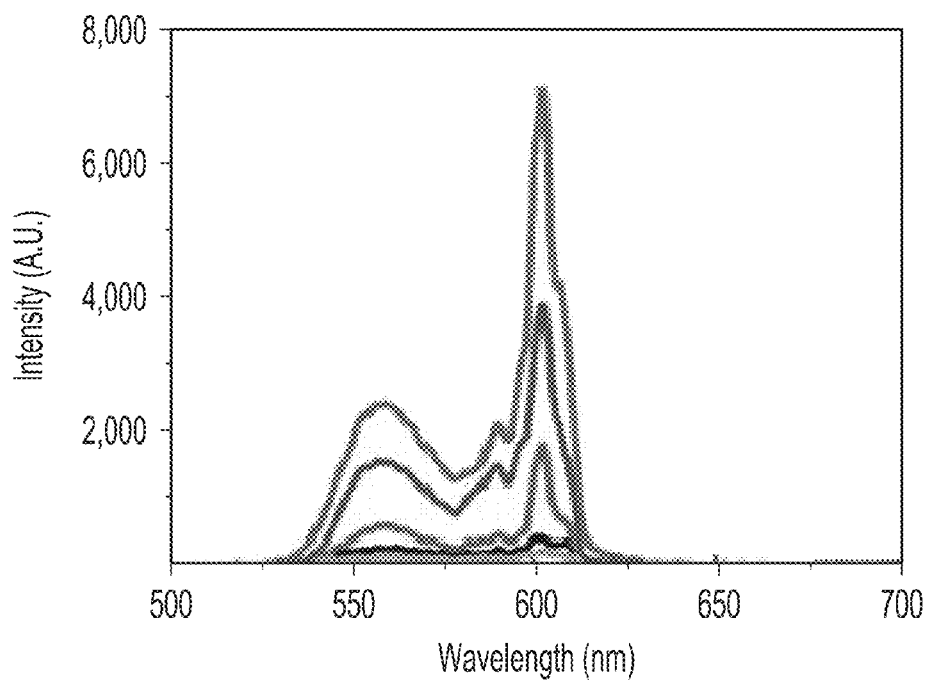
Figure 13D:
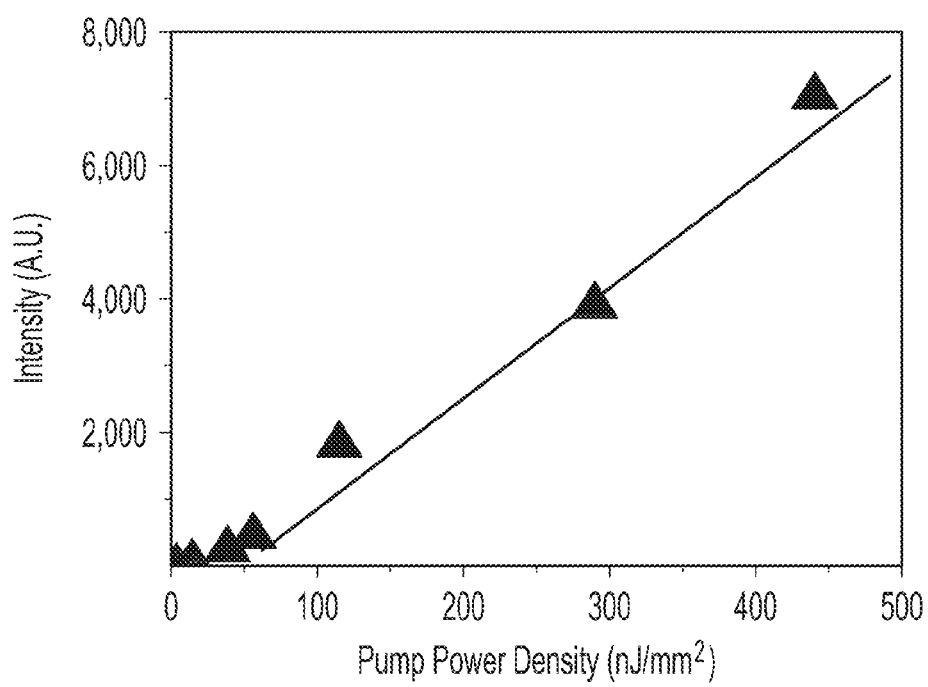
Figure 14A:
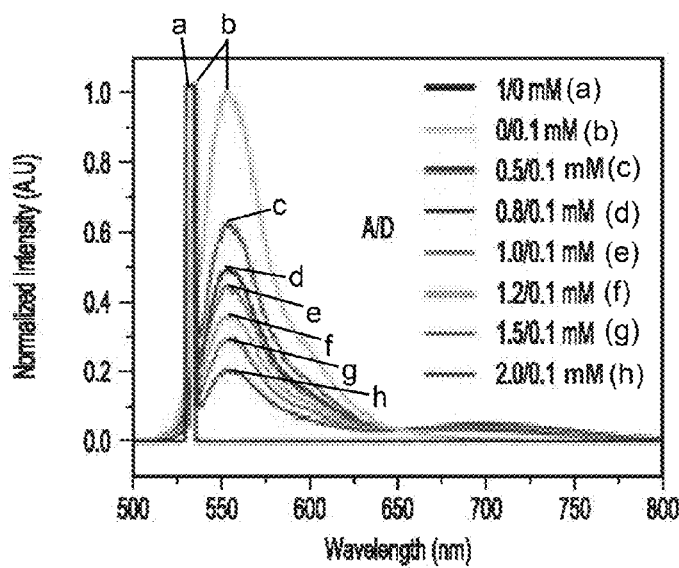
Figure 14B:
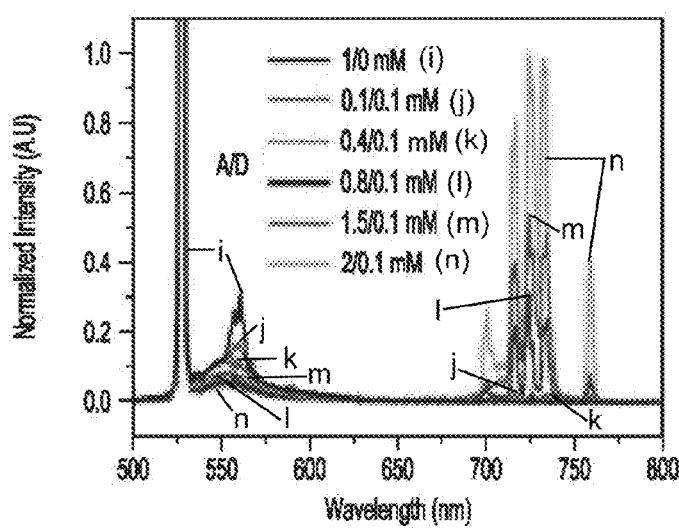
Figure 14C:
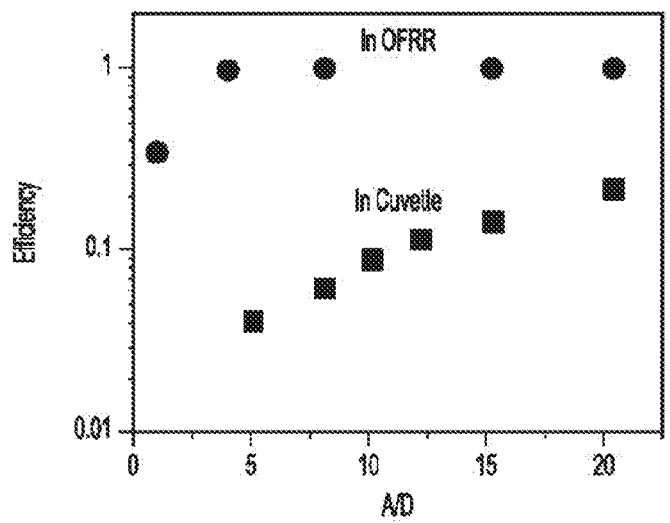
Figure 15:
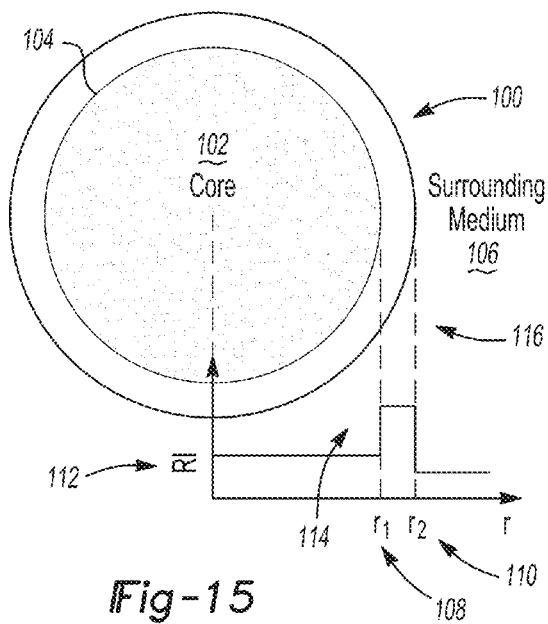
Figure 16:
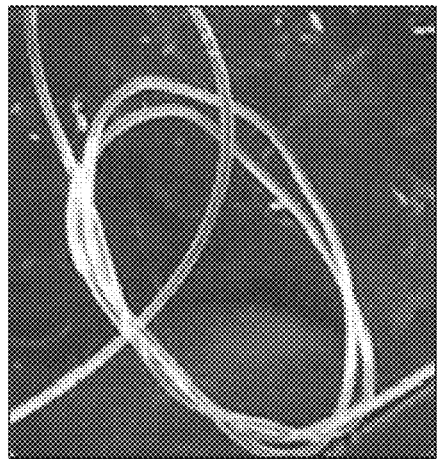
Figure 17A:
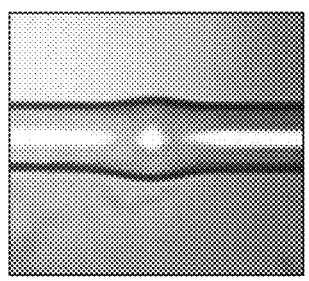
Figure 17B:
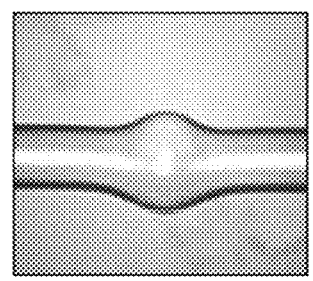
Figure 17C:
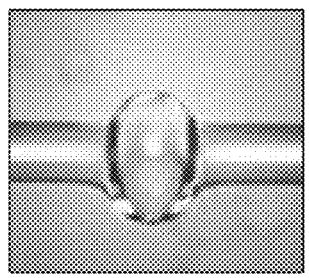
Figure 17D:
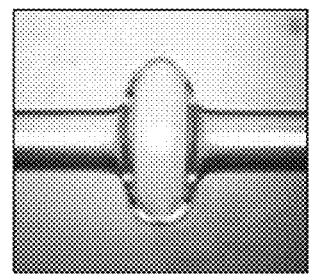
Figure 18A:
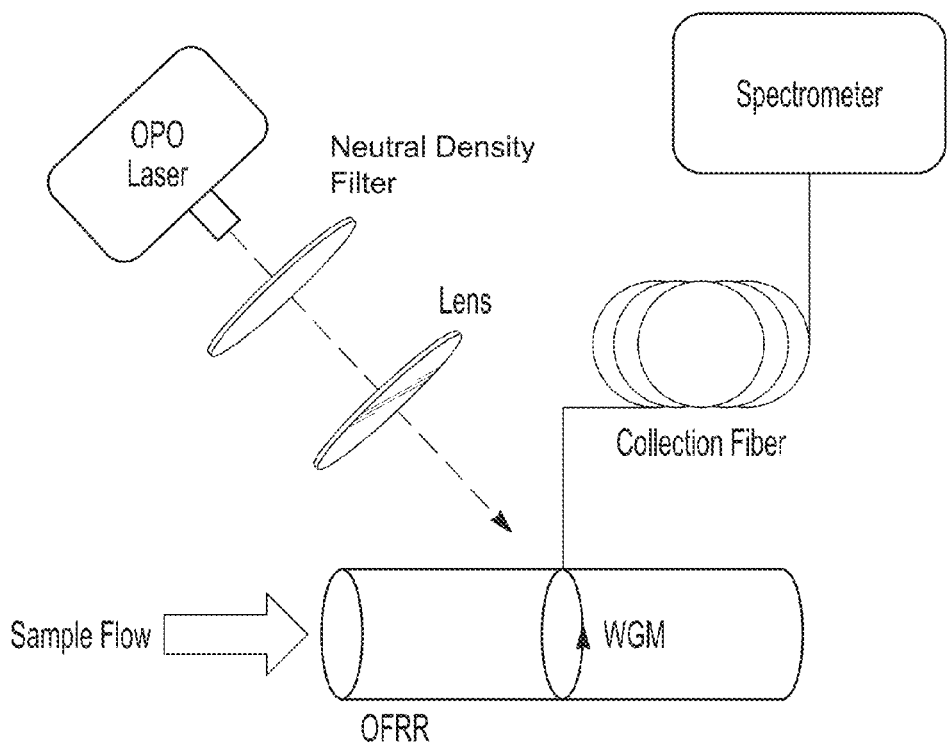
Figure 18B:
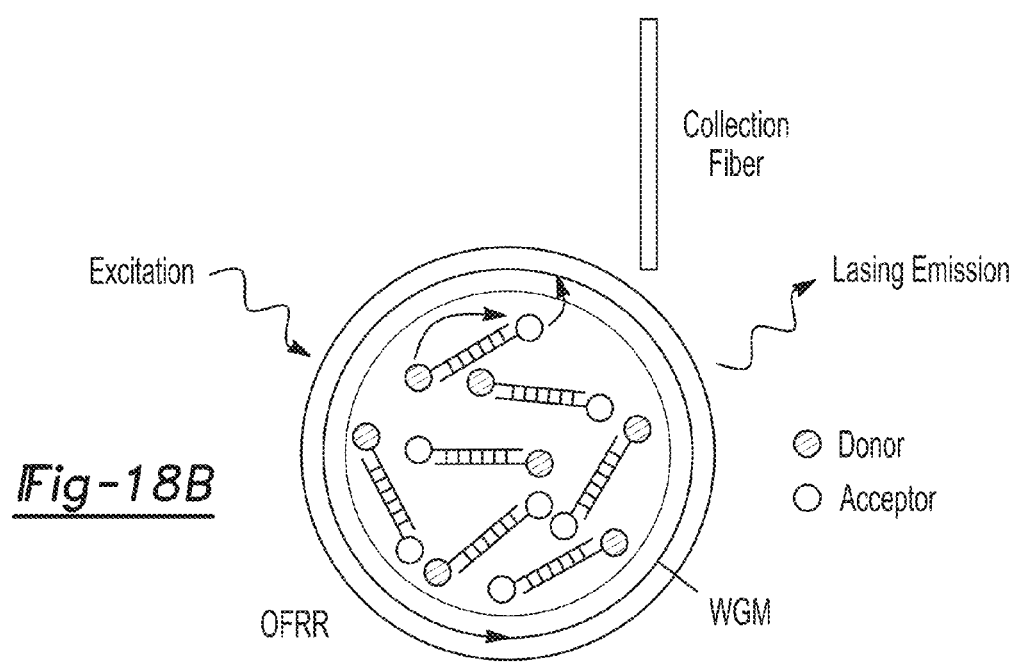
Figure 19:
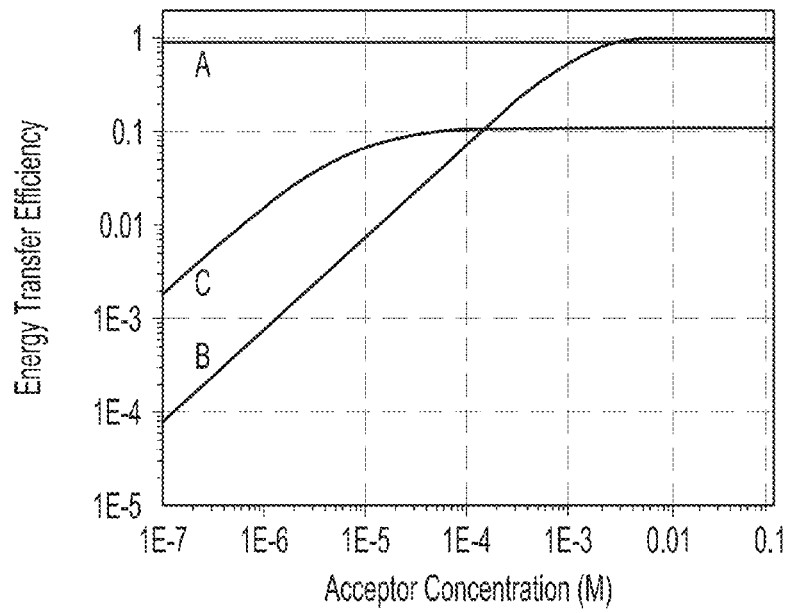
Figure 20A:
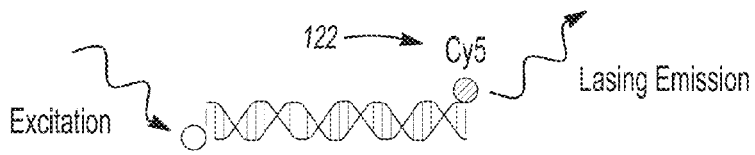
Figure 20B:
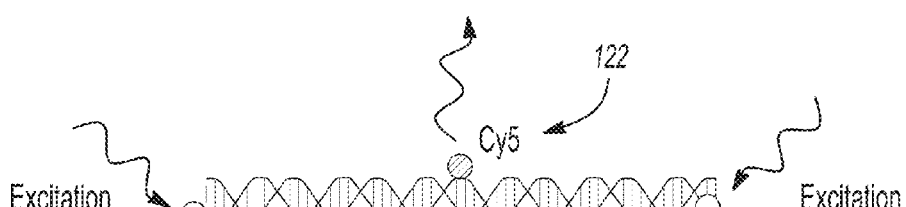
Figure 20C:
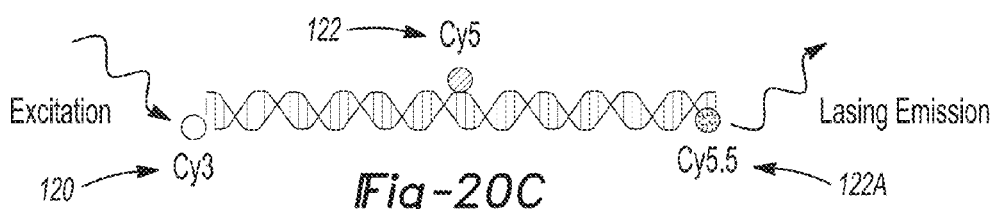
Figures 21A, 21B:
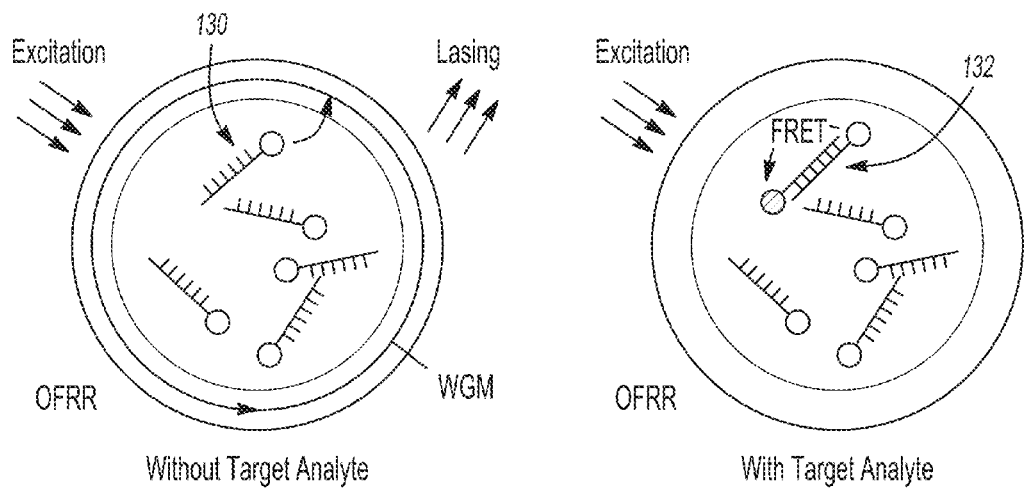
Figures 22A, 22B:
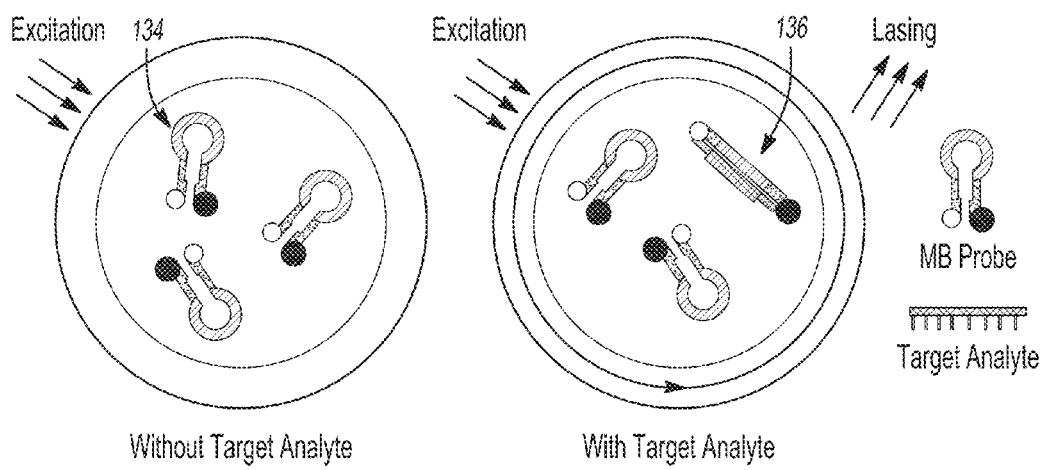
Figure 24A:
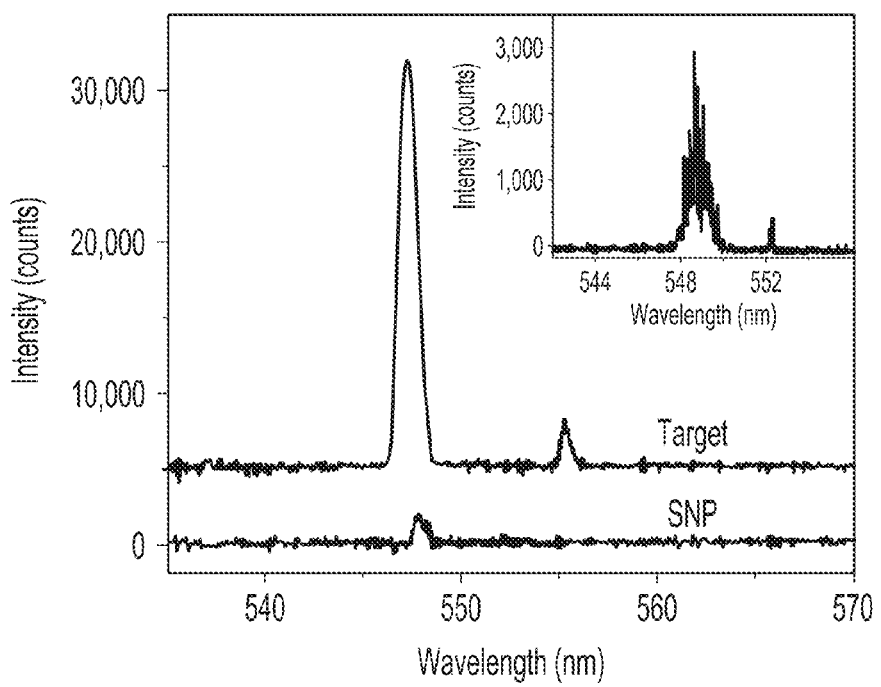
Figure 24B:
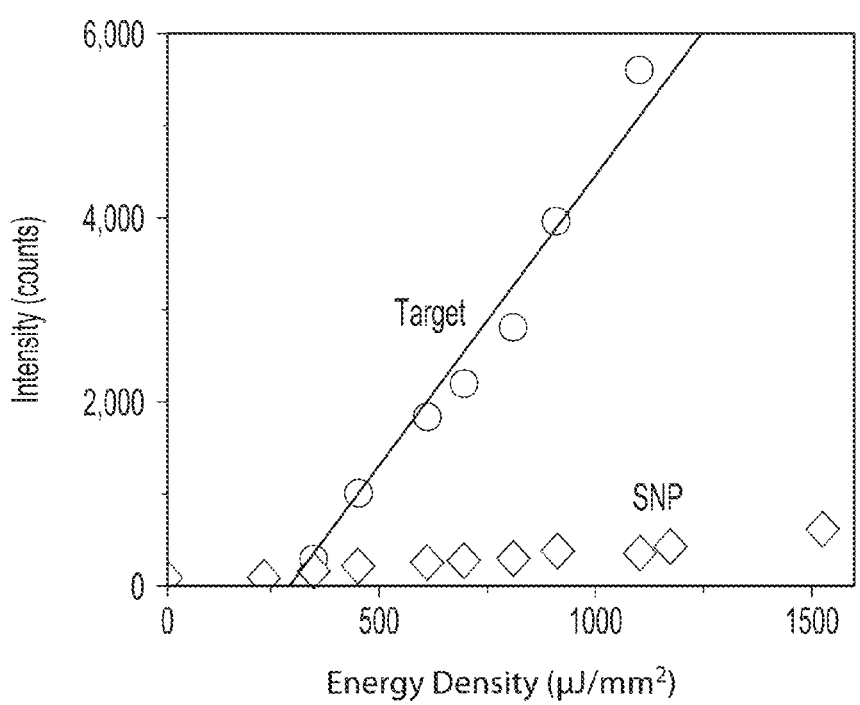

FIGS. 6A-6H illustrate various ring resonator configurations for optofluidic lasers; FIG. 6A depicts free falling liquid droplets generated by an orifice; FIG. 6B depicts liquid droplets generated by microchannels; FIG. 6C depicts liquid droplet formed on an ultrahydrophobic surface; FIG. 6D depicts fused silica microsphere immersed in gain medium; FIG. 6E depicts ring shaped waveguide formed on a chip; FIG. 6F depicts ring shaped liquid waveguide formed on a chip; FIG. 6G depicts ring resonator formed by a microfiber knot; and FIG. 6H depicts liquid cylindrical resonator formed with a capillary;

FIGS. 7A-7B illustrate an optofluidic ring resonator (OFRR) laser that can accommodate low retroactive index liquid; FIG. 7A depicts a cross section view and FIG. 7B depicts a side view;

FIG. 8 illustrates donors based on the present disclosure excited and transfer of energy to the acceptors within the ring resonators;

FIGS. 9A-9C depict DNA scaffolds based on the present disclosure; FIG. 9A depicts a Holliday structure; FIG. 9B depicts a 2-D crystal; and FIG. 9C depicts a tetrahedron structure;

FIGS. 10A-10B illustrate a non-limiting example of a WGM radial distribution for a thick-walled FIG. 10A and a thin-walled FIG. 10B capillary;

FIGS. 11A-11D are an exemplary embodiment according to certain aspects of the present disclosure; FIG. 11A depicts the OFRR fabrication setup; FIG. 11B depicts an OFRR made from a preform; FIG. 11C depicts SEM image of an OFRR; and FIG. 11D depicts a cross section image of tens of meters of OFRR;

FIGS. 12A-12D depict an exemplary embodiment of a Q-factor characterization; FIG. 12A depicts the OFRR with taper coupling; FIG. 12B illustrates two methods of detection of WGM spectral position; FIG. 12C illustrates the WGM spectral position from two detectors; and FIG. 12D illustrates the Q-factor measurement;

FIGS. 13A-13D depict an exemplary OFRR dye laser; FIG. 13A depicts the OFRR dye laser experimental setup; FIG. 13B illustrates a lasing emission through taper outcoupling collection, showing no fluorescence background; FIG. 13C depicts the laser emission spectra of the 2 mM R6G in ethanol collected through free space; and FIG. 13D illustrates peak intensity nm compared to pump power density;

FIGS. 14A-14C illustrate FRET energy transfer based on an exemplary embodiment; FIG. 14A illustrates FRET carried out in a regular cuvette; FIG. 14B illustrates FRET carried out in an OFRR microlaser; and FIG. 14C illustrates the energy transfer efficiency as a function of acceptor-to-donor ratio;

FIG. 15 is an exemplary three-layer model illustrated using the MIE theory;

FIG. 16 is an exemplary polymer coated OFRR with 4.5 µm wall thickness fabricated from draw tower;

FIGS. 17A-17D are exemplary depictions of bubble-shaped OFRRs;

FIGS. 18A-18B are an exemplary schematics comprising an OFRR-FRET microlaser;

FIG. 19 illustrates the FRET efficiency between Cy3 and Cy5 through a 13-base-pair DNA scaffold showing energy transfer efficiency for FRET between Cy3 and Cy5 in free solution and OFRR-assisted energy transfer efficiency between Cy3 and Cy5 cc;

FIGS. 20A-20C illustrate various DNA scaffolds based on the present disclosure; FIG. 20A is a 1:1 ratio of donor to acceptor; FIG. 20B is a 2:1 ratio of donor to acceptor; and FIG. 20C is a cascade of donor to acceptor;

FIGS. 21A-21B illustrate an exemplary embodiment of FRET turn-off sensor; FIG. 21A depicts a sensor original state where a lasing emission is from a probe of single stranded DNA (ssDNA); and FIG. 21B illustrates when target ssDNA is present, lasing emission from probe ssDNA is quenched due to the FRET between probe ssDNA and target ssDNA;

FIGS. 22A-22B illustrate an exemplary embodiment of molecular beacon (MB) FRET turn-on sensor; FIG. 22A depicts the sensor original state: No lasing emission from MB probe; and FIG. 22B depicts when target ssDNA is present, lasing emission obtained from MB;

FIGS. 23A-23C illustrate an exemplary embodiment of a saturation dye with single-stranded DNA or ssDNA (FIG. 23A) and double-stranded DNA or dsDNA (FIG. 23B). FIG. 23C is an exemplary embodiment of showing a schematic of the OFRR laser; and FIGS. 24A-24B illustrate the lasing spectra for target DNA and the SNP (FIG. 24A) and the lasing intensity (FIG. 24B).

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. Further, the present disclosure contemplates that any particular feature or embodiment can be combined with any other feature or embodiment described herein. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise.

The terms "comprises," "comprising," "including," and "having," are inclusive and therefore specify the presence of stated features, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

As referred to herein, the word "substantially," when applied to a characteristic of a composition or method of this disclosure, indicates that there may be variation in the characteristic without having a substantial effect on the chemical or physical attributes of the composition or method.

Throughout this disclosure, numerical values represent approximate measures or limits to ranges to encompass minor deviations from the given values and embodiments having about the value mentioned as well as those having exactly the value mentioned. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. If, for some reason, the imprecision provided by "about" is not otherwise understood in the art with this ordinary meaning, then "about" as used herein indicates a possible variation of up to 5% in the value.

As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

When an element or layer is referred to as being "on," "contacting," "engaged to," "connected to," or "coupled to" another element or layer, it may be directly on, engaged, contacting, connected, or coupled to the other element or layer, or intervening elements or layers may be present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, and the like may be used herein to describe various components, moieties, elements, regions, layers and/or sections, these components, moieties, elements, regions, layers and/or sections are not exclusive and should not be limited by these terms. These terms may be only used to distinguish one component, moiety, element, region, layer or section from another component, moiety, element, region, layer or section. Terms such as "first," "second," and other numerical terms when used herein do not imply a sequence or order unless clearly indicated by the context. Thus, a first component, moiety, element, region, layer or section discussed below could be termed a second component, moiety, element, region, layer or section without departing from the teachings of the example embodiments.

Spatially relative terms, such as "bottom," "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

In various aspects, the present disclosure provides new methods for detection of target analytes. In certain aspects, the present disclosure provides a method of detecting a target analyte, by binding the target analyte and a probe with at least one fluorophore to form a fluid composition. The method also comprises exciting a fluid composition within a laser cavity and measuring a laser emission from the fluid composition based on an interaction between the target analyte and the probe. In yet other aspects, the method provides hybridizing the target analyte and the probe, prior to the exciting.

In yet other aspects, the present disclosure provides a method for exciting a solution within a laser cavity, the solution comprising an acceptor fluorophore and a donor fluorophore, wherein a distance between the acceptor fluorophore and the donor fluorophore is sensitive to the analyte, measuring acceptor fluorophore emission and donor fluorophore emission, and detecting presence of the analyte based on the fluorescence resonance energy transfer (FRET).

Based on the present disclosure, a target analyte is a compound, particle, or other composition of interest to be detected from a fluid (e.g., liquid or gas). As used herein, the term "fluid" is intended to broadly encompass gases, liquids, vapors, semi-liquids, and suspensions of solids in liquids or gases. In certain alternative aspects, the present teachings may be employed to detect a target species from a fluid. Examples of target analytes include, without limitation, cells, drugs, hormones, polypeptides, antibody fragments, peptides, carbohydrates, single-stranded DNA (ssDNA), double-stranded DNA (dsDNA), RNA, oligonucleotides, single-nucleotide polymorphisms (SNPs), and proteins including immunoglobulins, polysaccharides, nucleic acids, and combinations thereof. For example, as will be discussed in further detail below, the inventive technology can be employed to detect biological target species, like genetic materials, proteins, polypeptides, biomolecules, viruses, saccharides, antigens, and the like from a fluid composition. Thus, in certain aspects, the present teachings are directed to methods for detecting a target species in a fluid composition. As used herein, the term "composition" refers broadly to a substance containing the target species, but which may also comprise additional species, substances, or compounds. Likewise, the term "material" also broadly refers to matter containing target species.

The techniques of the present disclosure can be used in sensitive bioanalytical assays to detect the presence and to quantify the concentrations of target analytes. In certain aspects, the methods of the present teachings detect the presence and quantify the concentrations of target analytes bound with specific binding reagents or biomarkers, for example. Therefore, the methods of the present disclosure have vast applicability for numerous applications and can be employed in novel biologic assays and separation devices. In certain aspects, the fluorophore (which may be more generally a chromophore) is a material that emits a predetermined wavelength of electromagnetic light energy in response to absorbing and being excited by light energy. In certain variations, the fluorophore is optionally a saturation dye, an acceptor fluorophore, a donor fluorophore or a fluorescent protein. An acceptor and a donor fluorophore can cooperate with one another, so when in close proximity to one another, excitation of a donor fluorophore results in energy transferring (e.g., via a non-radiative energy transfer mechanism) to the nearby acceptor fluorophore. Such a mechanism is used in fluorescence resonance energy transfer (FRET) detection. In various aspects, the acceptor fluorophore and the donor fluorophore are independently selected from the group consisting of: FAM, HEX, TET, JOE, NAN, ZOE, ROX, R110, R6G, LDS 722, TAMRA, Alexa Fluor dyes, Cy dyes, and combinations thereof. When the donor and acceptor bind together, energy transfer occurs, causing the decrease in donor fluorescence and increase in acceptor fluorescence. In certain aspects, the fluorescent dye may be an intercalating dye that can indicate the presence of dsDNA or ssDNA, by exhibiting distinct fluorescence emissions dependent on the intercalating dye's association with double-stranded or single-stranded DNA (by insertion into or association with the nucleic acid structure). In other variations, a donor fluorophore may be paired with a quencher acceptor, so that energy is transferred, but results in no light or EM emissions when the quencher acceptor material is in close proximity to the donor fluorophore.

In certain aspects, the fluorescent protein comprises: fluorescent protein (GFP), yellow fluorescent protein (YFP), and combinations thereof.

In various aspects, the saturation dye comprises SYTO 40 blue-fluorescent nucleic acid stain, SYTO 41 blue, SYTO 42 blue, SYTO 43 blue, SYTO 44 blue, SYTO 45 blue, a green-fluorescent SYTO dye, SYTO 9 green, SYTO 10 green, SYTO BC green, SYTO 13 green, SYTO 16 green, SYTO 24 green. SYTO 21 green, SYTO 27 green, SYTO 26 green, SYTO 23 green, SYTO 12 green, SYTO 11 green, SYTO 20 green, SYTO 22 green, SYTO 15 green, SYTO 14 green, SYTO 25 green, an orange-fluorescent SYTO dye, SYTO 86 orange, SYTO 81 orange, SYTO 80 orange, SYTO 82 orange, SYTO 83 orange, SYTO 84 orange, SYTO 85 orange, a red-fluorescent SYTO dye, SYTO 64 red, SYTO 61 red, SYTO 17 red, SYTO 59 red, SYTO 62 red, SYTO 60 red, SYTO 63 red, a Hoechst dye, Hoechst 33342, Hoechst 34580, Hoechst 33258, DAPI, LDS 751 and combinations thereof.

Figure 1:
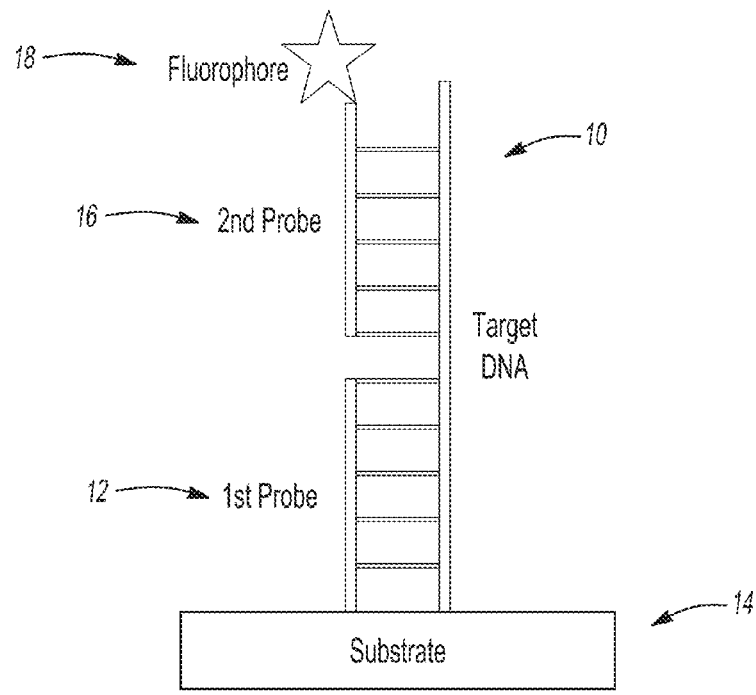
FIG. 1 illustrates conventional fluorescence based DNA detection.

FIG. 1 illustrates a fluorescence based detection of a target analyte 10 involves immobilization of a first probe 12 on a solid substrate 14, subsequent capture of a target analyte, buffer rinsing, and final introduction of a second probe 16 labeled with fluorophores 18 based on techniques known in the art. These processes ensure the detection specificity, as non-target DNA would not be able to bind to the probe after the buffer rinsing and therefore no fluorescence signal would be generated. However, probe immobilization and detection procedures can be time-consuming and costly. In addition, the existence of the solid substrate 14 reduces the mobility of the target analyte 10 relative to the probe and also deteriorates the probe's ability to efficiently capture the target analyte. Additionally, when detection of the target analyte occurs in free solution, this significantly simplifies the detection processes and allows for efficient and rapid analysis without any spatial confinement. However, free solution detection is unable to provide the needed detection specificity, as the fluorescence signal is generated indiscriminately regardless of the presence of the target analyte.

The present disclosure provides a method comprising exciting a fluid composition within a laser cavity and measuring a laser emission from the fluid composition based on an interaction between the target analyte and the probe. In various aspects, the interaction comprises an energy transfer, intercalation, hybridization of the target analyte and the probe, or a combination thereof. In certain aspects, the energy transfer comprises fluorescence resonance energy transfer (FRET) detection technology. In yet other aspects, the energy transfer comprises fluorescence resonance energy transfer (FRET), fluorescence resonance energy transfer (FRET) with a molecular-beacon, or cavity-assisted radiative energy transfer.

Fluorescence resonance energy transfer (FRET) is a technique for bio/chemical detection, drug discovery, and the study of structure and conformation of proteins and nucleic acids. In contrast to the simple fluorescence intensity measurement, FRET is highly specific, as the energy transfer occurs only when the target analyte binds to the probe so that the donor fluorophore and acceptor fluorophore are in close proximity. Additionally, the ratiometric measurement between acceptor and donor emission before and after the energy transfer significantly reduces the impact of variations in excitation sources. In various aspects, the present disclosure provides a method of detecting a target analyte, by labeling the target analyte with an acceptor fluorophore and labeling a probe with a donor fluorophore. After being labeled, the labeled target analyte and labeled probe are hybridized to form a fluid composition.

In various aspects, the energy transfer occurs when the acceptor fluorophore and donor fluorophore are within a certain proximity or distance to one another. Thus, in certain aspects, energy transfer may occur where the acceptor-labeled target analyte and the donor-labeled probe analyte are hybridized. In certain aspects wherein energy transfer occurs when the acceptor fluorophore and the donor fluorophore are separated by a distance of greater than or equal to about 1 nm to less than or equal to about 20 nm; when the target analyte hybridizes with the probe. As illustrated in FIGS. 2 and 3, FRET is a short-ranged non-radiative energy transfer process, in which the energy is transferred from the excited fluorescent donor molecule to the fluorescent acceptor 20 (FIG. 2) or non-fluorescent quencher 34 (FIG. 3) via resonant dipole-dipole interaction when donor 20 and acceptor/quencher 34 have sufficient spectral overlap and are spatially close to each other, such as for example within 1 to 10 nm. The energy transfer efficiency, E, is related to the Förster distance, $R_0$, and the donor-acceptor distance, R, by equation (1):

$$E = \frac{R_0^6}{R_0^6 + R^6}. \tag{1}$$

Figures 2A, 2B:
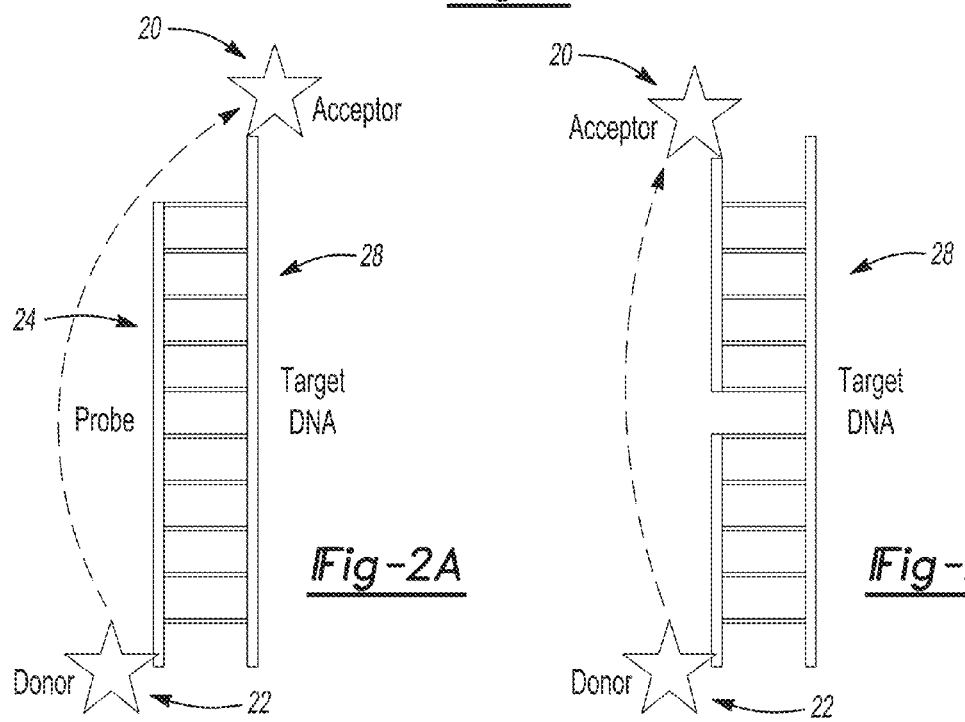
FIGS. 2A-2B illustrate DNA detection based on colorimetric fluorescence resonance energy transfer (FRET) in accordance with the present disclosure.

Because of its $1/R^6$ dependence, FRET is extremely sensitive to the distance between the donor 22 and acceptor 20. As illustrated in FIG. 2A, as a non-limiting example, DNA is detected using colorimetric FRET. The probe single-stranded DNA (ssDNA) 24 complementary to the target ssDNA 24 is labeled with a donor fluorophore 22, whereas the target ssDNA 28 is labeled with an acceptor fluorophore 20. In various aspects, when the complementary target ssDNA 28 hybridizes with the probe 24, the FRET signal may be generated, showing the increased acceptor emission and concomitant decreased donor emission (as shown in FIG. 4). For noncomplementary DNA, the donor and acceptor are far apart and no energy transfer occurs.

In other variations, an intercalating dye, such as a fluorescing intercalating dye, can indicate the presence of the target analyte. Such a target analyte may be a nucleic acid, like DNA. The intercalating dye can intercalate or insert into or otherwise associate with the target analyte (e.g., inserting between stacked base pairs), so that the intercalated dye provides a significant and detectable emission upon excitement as compared to the lower emissions of free dye in the surrounding environment.

In various aspects, the present disclosure provides an optical biosensing apparatus for detecting a target analyte, comprising: an optofluidic ring resonator (OFRR). The optofluidic ring resonator comprises a thin-walled fused silica microcapillary comprising a volume of the target analyte; and a laser cavity, wherein the target analyte is detected within the laser cavity based on an energy transfer. In certain aspects, in the present methods, energy transfer takes place in a laser cavity where a laser emission from the acceptor and concomitant donor emission quenching are observed. In other aspects, the laser cavity is an optofluidic ring resonator (OFRR) microlaser with an intracavity biosensing platform. The FRET signal (the ratio between the acceptor emission and donor emission) is much stronger than a conventional FRET signal and therefore, can be used for biosensing with higher sensitivity.

In certain aspects, the target analyte is detected within the laser cavity based on an interaction such as an energy transfer. In yet other aspects, the detection results from an enhancement in a sensing signal and significant suppression of the single-to-noise ratio. The OFRR is a capillary based ring resonator, which supports extremely high Q-factors for optofluidic lasers. When FRET takes place inside the OFRR laser, the detection paradigm is changed. The signal to noise may be improved due to the enhanced laser emission (i.e., signal) and suppressed fluorescence background (i.e., noise). The sensor device combines the advantages of detection sensitivity and selectivity, integrated microfluidics associated with capillaries, and low sample volume. In various aspects, the volume of the target analyte is greater than or equal to about 0.01 nL to less than or equal to about 12 nL. The technology may be used in broad applications, including for example, the analysis of DNA, microRNA, as well as other biomolecules. In various aspects, the target analyte comprises a protein, an enzyme, a receptor, a protein, an antibody fragment, a peptide, a carbohydrate, nucleic acids, single-stranded DNA, double stranded DNA, RNA, and oligonucleotide, a single-nucleotide polymorphism (SNP) sequence and any combination thereof. In non-limiting examples, various concentrations of target DNA can be used to test the sensing performance of these devices and they can be compared with existing FRET sensors. In various aspects, single-base mismatch detection can be performed with perfect matched sequences, single-nucleotide polymorphism (SNP) sequences, and a pool of random sequences, to demonstrate the selectivity of the present FRET sensors.

In other aspects, the target analyte is detected within the laser cavity based on an interaction such as hybridization the target analyte and the probe after being bound to saturation dye. Referring to FIG. 23A, the saturation dye does not have strong fluorescence by itself when there is only single-stranded DNA (ssDNA). Referring to FIG. 23B, The saturation dye specifically binds to the double-stranded DNA (dsDNA) and emits light strongly, thus for example, the target sample has bright fluorescence only when the ssDNA probe is hybridized with the complementary ssDNA target.

In various aspects the present technology relates to optofluidic ring resonator microlasers for ultrasensitive intracavity analysis. Various types of OFRR configurations can be used for the optofluidic laser. In various aspects, the configurations include a cylindrical OFRR and a bubble-shaped OFRR. For each configuration, the present disclosure establishes fabrication protocols, ways to optimize fabrication parameters, and describes how to characterize the optical properties (e.g., resonant modes, mode spatial distribution, Q-factors, and laser emission collection). Theoretical analysis can be used to guide the design of the OFRR to achieve the lowest possible lasing threshold.

In addition to the energy transfer format biosensing, the present methods use of the laser cavity with intracavity detection can be applied to the molecular beacon (MB) type of energy transfer. In MB, the probe is labeled with both donor fluorophore and acceptor quencher. In the absence of the target analyte, the donor emission is quenched due to the nearby quencher. In the presence of the target analyte, the donor and quencher are separated far apart and the fluorescence from the donor resumes. In the present technology, the MB detection takes place in a laser cavity. As a result, the lasing emission much stronger than fluorescence is obtained from the donor when the target analyte is present.

In certain variations, the method of the present invention provides an energy transfer based on FRET in the format of a molecular beacon (MB). As illustrated in FIG. 3, a MB 28 typically consists of a 25-35 base long nucleotide sequence with a complementary 5-6 base region (stem) 34 at the 5' and 3' end, to which a fluorophore and a nonfluorescent quencher are covalently attached. In its natural conformation, (as shown in FIG. 3A), the complementary ends hybridize and MB forms a hairpin shape with the fluorophore 30 and quencher 32 in close proximity. The fluorophore fluorescence 30 is quenched by the quencher 32 through efficient FRET. As illustrated in FIG. 3B, as a non-limiting example, in the presence of a target DNA 36, the loop strand of the MB 28 hybridizes with the complementary target sequence, causing the stem 34 to open. As a result, the fluorophore 30 and quencher 32 are far apart and the fluorescence is restored. Because of this feature, MB may also be referred to in the art as "turn-on FRET." The MB generates a fluorescence signal proportional to the amount of target analytes present and allows for the detection of unlabeled DNA. As illustrated in FIG. 4, colorimetric FRET, leakage is reflected in the tail of the donor emission present in the acceptor emission band, whereas in MB it arises from the incomplete fluorescence quenching in the hairpin form. This leaked emission acts as a high level of background and greatly limits the detection sensitivity.

In yet other aspects, the energy transfer comprises a cavity-assisted radiative energy transfer. The cavity-assisted radiative energy transfer occurs when the emission from the donor is first coupled into the cavity, which stores photons for an extended amount of time before they are re-absorbed by the acceptor. The cavity-assisted transfer efficiency is determined by the fraction of donor emission into cavity modes and the probability of acceptor re-absorption. Since the cavity-assisted energy transfer does not require that the donor and acceptor be in close proximity, it generates a non-specific signal.

In various aspects of the present technology of energy transfer may be controlled by DNA scaffolds. These include an OFRR-FRET laser with a gain medium composed of single-stranded DNA (ssDNA) and organic dye molecules. The donor and acceptor dye molecules are conjugated with complementary ssDNA, respectively, where, upon hybridization, the efficient energy transfer occurs to support the acceptor lasing. In various aspects the target analyte is hybridized with the acceptor fluorophore and the at least one probe is hybridized with the donor fluorophore in a solution. The lasing properties (such as the emission intensity and threshold) can be sensitively controlled by the DNA scaffold, which plays an important role in the FRET process taking place in a high-Q microcavity. FRET lasing can be achieved even at dye concentrations in the sub-micromolar range.

In other aspects, the present disclosure provides a biosensing apparatus for detecting a target analyte. A variety of sensing or detector apparatuses may be used, including a variety of known cavity or resonator structures used for detecting target analytes. In certain variations, the biosensing apparatus is an optic biosensing optofluidic ring resonator (OFRR) for detecting a target analyte. The optofluidic ring resonator comprises a volume of the target analyte, a thin-walled fused silica microcapillary, and a laser cavity, wherein the target analyte is detected within the laser cavity based on an energy transfer. Based on the present technology, optofluidic microlasers may be used for lab-on-a-chip and compact on-chip light sources in which photonics and microfluidics are integrated to achieve new functionalities. As compared to traditional liquid lasers (such as dye lasers), optofluidic microlasers are smaller in size, safer to operate, and consume less sample. Optofluidic microlaser cavities can be used with embedded distributed feedback (DFB) gratings, circular Bragg gratings, and Fabry-Pérot-type resonators. However, all of these designs have relatively low Q-factors (on the order of about $10^3$), which leads to a high lasing threshold on the order of 10 µJ/mm².

Optical ring resonators may also be employed for optofluidic laser development. In a ring resonator, the whispering gallery modes (WGMs) form at the boundary of high and low refractive index (RI) media, as shown in FIG. 5. The WGMs 38 circulate along the ring resonator 40 and interact with the surrounding medium and usually has much higher Q-factors than other types of optical cavities, thus providing excellent optical feedback to achieve low lasing threshold.

FIG. 6 illustrates ring resonator configurations known in the art that may be used for optofluidic lasers. Microdroplets, (FIG. 6A-6C) have high Q-factors ($\sim 10^8$) and have been extensively studied in the past decades. Solid microspheres are illustrated in FIG. 6D. Solid or liquid ring-shaped waveguides (FIG. 6E-6F)). Microfiber knot based ring resonators are illustrated in (FIG. 6G). FIG. 6H shows another ring resonator configuration, in which a regular glass capillary with a wall thickness over 30 micrometers is used.

As a non-limiting example, the present methods, systems, and apparatus include optofluidic ring resonator (OFRR) microlaser technology that can accommodate a low RI liquid such as water or buffer for DNA analysis. As illustrated in FIGS. 7A-7B, the OFRR 42 can employ a piece of thin-walled fused silica capillary 44. In various aspects, the thin-walled fused silica microcapillary has an outer diameter of greater than or equal to about 10 µm to less than or equal to about 1,000 µm and a thickness of less than or equal to about 10 µm. FIG. 7A illustrates a circular cross section of the capillary 44 forms the ring resonator 40 that supports the WGMs of high Q-factors. In various aspects, the Q-factors are greater than $10^7$. The capillary wall is relatively thin so that the WGMs are exposed to the core. In various aspects, a penetration depth of the WGMs is about 100 nm. The WGMs interact with the gain medium 46 in the liquid passing through the capillary, and provide the excellent optical feedback for low-threshold lasing. Additionally, the laser emission can easily and highly efficiently be coupled out via a guide 48, such as an optical fiber, a fiber prism, or a waveguide in contact with the OFRR 42. Furthermore, the OFRR integrates naturally with the fluidics inherent to capillaries, thus exhibiting fluid handling capability and allowing for approximately 1,000 times reduction in sample detection volume. In various aspects, the volume of the target analyte is greater than or equal to about 0.01 nL to less than or equal to about 12 nL. The OFRR of the present technology may be fabricated easily and cost-effectively using a capillary pulling station or a fiber draw tower.

In various aspects, the present disclosure provides a method of detecting a target analyte, by labeling the target analyte with an acceptor fluorophore and labeling a probe with a donor fluorophore. After being labeled, the labeled target analyte and labeled probe are combined and optionally hybridized to form a fluid composition. In various aspects, a method of detecting a target analyte comprises exciting a fluid composition.

The OFRR dye microlaser can be excited directly by tuning the pump laser wavelength into the dye absorption band. Alternatively, it can also be excited indirectly through FRET, in which dye mixtures, composed of the donor and the acceptor, are used. As illustrated in FIG. 8, donors are excited by the pump laser 50 and subsequently transfer energy to acceptors for lasing 50. The FRET process can drastically change the microfluidic laser properties 52. It significantly extends the laser emission wavelength range without the need to change the pump laser wavelength. Moreover, energy transfer based dye lasers have a much higher pump efficiency and lower lasing threshold than the corresponding single dye lasers due to the low donor absorption loss at the acceptor lasing wavelength.

Since the FRET efficiency has a sixth power inverse dependence on the donor and acceptor distance, as illustrated in Eqn. (1), the donor and acceptor distance is important to the FRET process, hence the lasing properties; e.g., gain profile, lasing spectrum, energy conversion efficiency, and lasing threshold. In the energy transfer based dye lasers reported to date, donor and acceptor fluorophores are homogenously distributed in free solution. Therefore, the average distance between donor and acceptor can only be statistically determined from the donor and acceptor concentrations.

This leads immediately to two undesirable consequences. First, lack of precise control over the donor and acceptor distance makes it difficult to study the FRET process in a laser cavity. Second, in order to have a FRET efficiency higher than 50%, the donor and acceptor distance needs to be within the Förster distance (1 to 20 nm), which translates to a donor and acceptor concentration in the millimolar range. However, the FRET lasing of such a high concentration has virtually no use in any biomedical applications, since many biological samples can have a concentration a few orders of magnitude lower than millimolar. Additionally, high concentration organic dye solution can only be achieved with organic solvent such as ethanol. FRET lasing has not been demonstrated with an organic buffer solution in which biological samples are usually dissolved.

In order to address these issues, various aspects of the present technology employ DNA scaffolds to achieve FRET lasers. Through a DNA scaffold, the donor and acceptor distance and spatial configuration can be precisely controlled. In various aspects, the acceptor fluorophore and the donor fluorophore are separated by a distance of about 1 to about 20 nm; when the target analyte hybridizes with the probe. on the DNA scaffold. High FRET efficiency can be obtained regardless of the donor and acceptor concentration. In these aspects, the donor and acceptor can be conjugated with complementary ssDNAs, respectively. Through DNA self-assembly technology, various types of biostructures, as exemplified in FIGS. 9A-9C, can be realized, which allow characterization of the FRET process in a cavity and determination of how nonlinear lasing properties are affected by FRET. Such biostructures are a Holliday structure, a 2-crystal structure, and a tetrahedron structure.

Intracavity DNA analysis based on FRET lasing can include the following aspects. In certain aspects, a method of detecting a DNA molecule is provided that comprises: labeling a target, such as a DNA molecule with an acceptor fluorophore and labeling at least one probe with a donor fluorophore. After labeling the hybridized DNA molecule and the hybridized probe are mixed to create a fluid composition, wherein upon hybridization the acceptor fluorophore and the donor fluorophore are separated by about 10 to about 30 base pairs. The method also comprises exciting the fluid composition within a laser cavity, measuring the acceptor fluorophore emission and the donor fluorophore emission with in the fluid composition and detecting the target analyte based an energy transfer between the acceptor fluorophore and the donor fluorophore, wherein the energy transfer is fluorescence resonance energy transfer (FRET).

The traditional fluorescence based biosensor uses a linear transduction signal, that is, the fluorescence intensity is linearly proportional to the absorption coefficient and quantum yield of the fluorophore labeled on the target macromolecules. The sensing signal consequently becomes too weak to be detected when a trace quantity of target analytes is present among large amount of non-target analytes. However, in contrast to the linear transduction signal, the fluorescence from fluorophores using intracavity DNA analysis based on FRET lasing can be amplified by the high-Q optical cavity into a nonlinear lasing emission signal. The lasing emission intensity, I, builds up exponentially as light propagates in a cavity with an inverted excited state population, given by, $I=I_0 \exp(gz)$, where $I_0$ is the fluorescence emission intensity from the dye molecule, g is the cavity gain coefficient, and z is certain distance within the cavity, respectively. If the presence of a target analyte can perturb the gain coefficient, it will lead to an exponential change in the laser output. Therefore, the sensing signal can be amplified exponentially through nonlinear lasing processes.

In yet other aspects, the present disclosure provides a method of detecting a DNA molecule, the method comprising combining a single-stranded DNA molecule and a single-stranded probe with a saturation dye to form a fluid composition, exciting the fluid composition within a laser cavity and measuring a laser emission from the fluid composition based on an interaction between the single-stranded DNA and the single-stranded probe.

Based on the present technology, building an intracavity biosensor may include the following aspects: (1) introduction of the target analyte into the laser cavity as an active part of the cavity gain medium to create a change; and (2) the activity of the target analyte should be able to perturb the lasing gain coefficient. In various aspects, the methods of detecting a target analyte may further comprise exposing the target analyte to an activity that causes a detectable change in the target analyte. In yet other aspects, the detectable change can be binding, dissociation, enzymatic cleavage, or a conformational change. With the inherent integration of microfluidics and high Q-factor optical cavity into one piece of capillary, the OFRR dye laser can be used for an intracavity high gain biosensor. As a non-limiting example, DNA detection can be used as a model system to demonstrate the sensing performance of the OFRR-FRET laser.

The present technology provides several non-limiting benefits. From the bio/chemical sensing point of view, the signal transduction through nonlinear optical response (i.e., lasing) is ground breaking. The signal intensity can be amplified exponentially, which enables ultra-sensitive intracavity detection capability. The OFRR microlaser platform can be implemented as a high-throughput, ultra-small sample consumption, ultra-high sensitivity, and high specificity bio/chemical sensor for potential clinical DNA transfer based dye laser that is able to work at very low dye concentrations with high energy transfer efficiency. In certain aspects, fluid composition comprises an organic buffer such as DNA hybridization buffer (0.5 M NaCl, 50 mM HEPES, pH 8.3, 0.2 mM EDTA), PBS (Phosphate buffered saline) buffer, tris-EDTA and combinations thereof. Furthermore, the dye laser can be used in a buffer solution instead of an organic solvent solution, which opens the door for use of the dye laser in many other bio/chemical applications.

In certain aspects, the energy transfer occurs on an integrated OFRR array integrated onto a wafer. The present technology provides a novel FRET laser sensing platform for ultrasensitive DNA analysis. The present technology can be further applied by integrating OFRR arrays onto a PDMS or silicon wafer based chip to develop a highly portable point-of-care device.

The following specific examples are provided for illustrative purposes of how to make and use the compositions and methods of this technology and, unless explicitly stated otherwise, are not intended to be a representation that given embodiments of this technology have, or have not, been made or tested.

EXAMPLES

Example 1

Theoretical Simulation of WGM in OFRR

A Matlab program based on the Mie theory can be used to calculate the WGM radial distribution in a cylindrical OFRR, an example of which is shown in FIGS. 10A-10B. When the wall is thick (FIG. 10A), the electric field has virtually no presence in the capillary core. Therefore, no laser can be observed for a thick-walled capillary due to the inefficient interaction between the WGM and the gain medium. In contrast, when the capillary wall becomes thinner, the WGMs of high Q-factors are exposed to the core (penetration depth about 100 nm; see FIG. 10B inset), interacting with the gain medium passing through the OFRR, and providing the optical feedback for lasing. The RI for the core is 1.33 and the RI for the wall is 1.45. Different OFRR geometries (including a bubble-shaped capillary) can be used to optimize the interaction between the electric field and the gain medium in particular aspects.

Fabrication of the OFRR

Since particular aspects of thin-walled capillaries are not commercially available, a computer-controlled pulling station has been assembled at the University of Michigan (Ann Arbor, Mich.) (see FIG. 11A) capable of fabricating an OFRR up to 50 centimeters in length (FIG. 11B) by rapidly stretching a fused silica preform under $CO_2$ laser irradiation. Specifically, two $CO_2$ lasers are used on opposite sides to provide more evenly distributed heating. Two ends of the tubing perform are mounted on the feed-in stage and pulling stage, respectively. Under $CO_2$ laser irradiation, the pulling stage is moved quickly away from the heating zone while the feed-in stage is slowly pushed toward the heating zone, keeping a relative constant mass of glass in the heating zone. The whole apparatus is enclosed into an acrylic box to reduce the air fluctuation to the laser heating zone on the capillary during pulling.

As the OFRR wall thickness is important to its optical properties, attention must be given to the temperature and pulling speed, as these parameters determine the ultimate diameter and wall thickness after pulling. Therefore, the optimized $CO_2$ power, feed-in speed, and pulling speed are obtained by trial and error for different tubing preforms. With different geometries of tubing preforms, an OFRR can be fabricated in a variety of sizes (e.g., OD in the range of 50-150 µm) with a wall thickness of about 5 µm (see FIG. 11C).

The OFRR can also be fabricated using an industrial fiber draw tower (see cross-sectional view of the OFRR in FIG. 11D). Currently this method is being employed with OFS Laboratories (Norcross, Ga.). Using OFS facilities, the OFRRs of kilometers in length can be fabricated. For example, a bubble-shaped OFRR can be fabricated using the industrial fiber draw tower. The outer diameter is 125 µm and the wall thickness is 4.5 µm.

Characterization of the Q-factor

A schematic of the Q-factor characterization setup is illustrated in FIGS. 12A-12D. Light from a tunable diode laser (JDS Uniphase, center wavelength 1550 nm) is coupled into the WGMs through the evanescent coupling by an optical fiber taper (as shown in FIG. 12A) in contact with the OFRR exterior surface. The tunable diode laser is periodically scanned across a small wavelength range of 110 pm while Detector #1 at the end of the fiber taper measures the optical intensity. As shown in FIG. 12B, when the laser wavelength matches the WGM resonant condition, $\lambda=2\pi r n_{eff}/m$, where r is the OFRR outer radius, $\lambda$ is the resonant wavelength, m is an integer, and $n_{eff}$ is the effective refractive index experienced by the WGM, respectively, the light couples into the OFRR and causes the measured transmission intensity to drop, leaving a spectral dip at Detector #1. In the meantime, the light coupled into the OFRR is scattered off the OFRR surface and can be detected as a spectral peak with a detector placed above the OFRR (Detector #2). Both the measured signals can be used to indicate the WGM spectral position as demonstrated in FIG. 12C. For example, the first approach can be easy to implement while the second scheme can be more suitable for an OFRR array, since detection essentially becomes taking an image of the array.

After a transmission spectrum is obtained for OFRR, the Q-factor for individual resonant mode can be calculated as $Q=\lambda/\Delta\lambda$, where $\lambda$ is the WGM resonant wavelength, and $\Delta\lambda$ is the full width measured at half maximum (FWHM) of the intensity. A WGM Q-factor of $10^7$ is shown in FIG. 12D. The high Q-factor is excepted since the OFRR is fabricated under high temperature, therefore the surface is extremely smooth.

OFRR Microlasers and Out-Coupling Via a Fiber Taper

In various aspects, an OFRR dye microlaser can use a single dye solution under direct pump laser excitation as illustrated in FIG. 13A-13D. Illustration of an OFRR dye microlaser setup is shown in FIG. 13A. A pulsed optical parametric oscillator (OPO, 532 nm and 5 ns pulse width) laser is used to excite 2 mM R6G dye in ethanol (RI=1.36) as the gain medium. The dye emission is collected either through free space or through an optical fiber taper and then sent to a spectrometer. With increased pump laser power till above lasing threshold, strong lasing emission emerges above the fluorescence baseline, which is shown in FIG. 13C. However, the lasing emission out-coupled through optical fiber taper shows no fluorescence background (FIG. 13B) compared with the lasing emission collected in free space (FIG. 13C). The fluorescence background cannot enter the WGM (rejection ratio of about $10^5$) and thus will not be transmitted through the fiber. Therefore, with taper outcoupling, the signal to noise ratio is greatly increased. The suppression in the signal to noise ratio is illustrated by the threshold curve measured to be around 25 nJ/mm² for the 600 nm peak in FIG. 13D, which is around 1,000 times lower than that of the state-of-the-art microfluidic dye lasers due to the extremely high Q-factors of the OFRR. The peak intensity is at 602.5 nm.

OFRR Microlaser Through FRET

In order to test the concept of energy transfer based lasing through FRET, a mixture of R6G and LDS 722 methanol solution is used as the donor and acceptor, respectively, as the gain medium. The FRET lasing spectrum is demonstrated in FIG. 14B, showing strong lasing emission in the acceptor fluorescence emission wavelength range. For comparison, FRET was carried out in a regular cuvette (FIG. 14A) and in an OFRR microlaser (FIG. 14B) under otherwise the same conditions. It can be clearly seen that in an OFRR the decrease in the donor emission and the increase in the acceptor emission become much more significant than their counterparts in a cuvette. This phenomenon arises from the nonlinear lasing action in both donor and acceptor. Whereas in a regular FRET, the addition of the acceptor reduces the donor fluorescence by $\Delta G$, the donor laser emission will be changed by approximately $\exp(\Delta G)$. As a result, any slight change in the donor or acceptor side will be drastically amplified by the laser process. FIG. 14C shows a quantitative comparison between the FRET in a cuvette and in an OFRR. The formula used, $\gamma=1/(1+I_D/I_A)$, where $I_D$ ($I_A$) is the donor (acceptor) emission intensity, to characterize the effective photon conversion efficiency from the donor to the acceptor. $\gamma$ or $I_A/I_D$ is usually used as the sensing signal. Based on this result, the sensing signal may be increased over 20-fold when A/D=5. At a lower A/D, the enhancement can be even larger. Through the enhancement in the sensing signal and significant suppression in the fluorescence leakage background, the intracavity FRET sensor is able to achieve unprecedented SNR for ultrasensitive detection of biomolecules.

Analysis, Fabrication, and Characterization of OFRRs.

Theoretical Analysis of the OFRR Dye Microlaser

Theoretical analysis and modeling of the OFRR dye microlaser can be used in determining the optimal design parameters to achieve the lowest possible lasing threshold. In an OFRR, WGMs reside in both the core and wall. Therefore, only a fraction of the WGM interacts with the gain medium. The lasing behavior of this partially interacting system can be analyzed by $I \propto 1/(\eta Q_0)$, where I is the lasing threshold, q is the fraction of the WGM in the core, and $Q_0$ is the empty cavity Q-factor when the ring resonator is filled with the solvent in the absence of dye. To lower the lasing threshold, a larger $\eta Q_0$ is required, which can be achieved by increasing the fraction of the light in the core, $\eta$, and/or by increasing $Q_0$.

The WGM of the OFRR can fully be described using Mie theory by considering a three-layered radial structure, as shown in FIG. 15. The radial distribution of the WGM electrical field of an OFRR 100 is governed by:

$$E_{m,l}(r) = \begin{cases} AJ_m(k_{m,l}n_1 r) & (r \leq r_1) \\ BJ_m(k_{m,l}n_2 r) + CH_m^{(1)}(k_{m,l}n_2 r), & (r_1 \leq r \leq r_2) \\ DH_m^{(1)}(k_{m,l}n_3 r) & (r \geq r_2) \end{cases}$$

where $J_m$ and $H_m^{(1)}$ are the $m^{th}$ Bessel function and the $m^{th}$ Hankel function of the first kind, respectively. The refractive index of the core 102, wall 104, and the surrounding medium 106 is described by $n_1$, $n_2$, and $n_3$. The terms $r_1$ and $r_2$ 108, 110 represent the inner and outer radius of the OFRR, respectively, and $k_{m,l}$ is the amplitude of the wave vector in vacuum for the $l^{th}$ order radial WGM. Using this three-layer model, the WGM spectral position, the radial distribution of the light, and $Q_{rad}$ can be obtained as a function of wall thickness, the OFRR size, operating wavelength, etc. Using the in-house simulation Matlab codes, the effects of different wall thickness, surrounding medium RI 114, 116, core RI 112, and different OD on the lasing threshold for a given gain medium can be determined and the optimal parameters for the OFRR can be found.

OFRR Fabrication

In various aspects, the OFRR of the present disclosure may include a cylindrical OFRR and a bubble-shaped OFRR. The OFRR fabrication is carried out in collaboration with OFS Laboratories (Norcross, Ga.).

Cylindrical OFRR

The OFRR can be fabricated with a wall thickness of 4-5 μm. In addition, OFRRs can be fabricated that are tens of meters long with outer diameters of about 100 μm and wall thicknesses of about 2 μm by using the fiber draw tower at OFS Laboratories (Norcross, Ga.). A thinner wall is desired to increase the fraction of the WGM in the core. Various sizes of preforms with different aspect ratios (outer diameter vs. wall thickness) and pulling speeds can be used. In addition, the preform may be pressurized to avoid heat-induced collapsing that reduces the aspect ratio. For example, capillaries with sub-micrometer wall thickness have been fabricated using the pressurization approach. Since the capillary becomes more delicate with the decreased wall thickness, the capillary can be coated in-situ with a layer polymer using industrial standard optical fiber coating polymer and procedures. This polymer coating can increase mechanical strength of the capillary (see FIG. 16) so that the capillary can be more easily handled and shipped. Multiple batches of OFRRs with the same design parameters can be fabricated in order to determine whether variations in size and wall thickness exist. The OFRR geometry can be characterized using a scanning electron microscope (SEM) to ensure that they are fabricated as designed.

Bubble-Shaped OFRR

Bubble-shaped OFRR can introduce light confinement along the capillary axial direction and improve the Q-factor of the ring resonator for a lower lasing threshold. Fabrication of the bubble-shaped OFRR can be based on the cylindrical OFRR using $CO_2$ lasers while pressurizing the sealed cylindrical OFRR and rotating it for a more evenly heating. The bubble-shaped OFRR can be fabricated with various curvatures (see FIG. 17). The bubble wall thickness can be less than 1 μm, as determined by SEM characterization. The bubble fabrication procedure can be optimized by adjusting the pressure, $CO_2$ laser power and exposure time, and the rotation speed to make bubbles of the desired size, curvature, and wall thickness.

OFRR-Fiber System Q-Factor Characterization

Both cylindrical OFRR and bubble-shaped OFRR can be characterized in terms of Q-factor and fraction of light in the core, as these two parameters are directly related to the lasing performance. For Q-factor characterization, a tunable diode laser at the wavelength of interest (e.g., 680 nm) is coupled into the OFRR through a tapered optical fiber (see FIG. 11). The Q-factor can be calculated by measuring the full-width-at-half-maximum (FWHM) of the spectral dip (see FIG. 12) at the taper output. The fraction of light in the core, q, can be estimated by measuring the WGM's sensitivity, S, i.e., its spectral shift in response to the RI change in the core RI. $\eta$ is related to S by: $\eta = Sn_{eff}/\lambda$, where $n_{eff}$ and $\lambda$ are the effective RI and the wavelength of the WGM of interest. To measure S, the core RI can be varied by mixing two liquids of different RI and WGM shift will be measured by scanning a tunable diode laser.

Development of OFRR-FRET Microlasers Controlled by DNA Scaffolds.

High efficiency FRET lasing can be achieved at low concentrations (i.e., sub-micromolar) of donor and acceptor in buffer solution via DNA scaffolds. The experimental design and method is as follows. The experimental setup is shown in FIGS. 18A-18B, where pump light from an optical parametric oscillator (OPO) laser can be loosely focused to illuminate a small segment of the OFRR capillary. FIGS. 18A and 18B both show excitation in the OFRR capillary by applying laser energy. FIG. 18B is a cross-sectional detailed view of the OFRR capillary component of the detection apparatus shown in FIG. 18A. Organic dye labeled DNA samples can be flowed through the capillary by a syringe pump at a flow rate of about 1 μL/min. Thus, in FIG. 18B, excitation by laser energy results in a lasing emission that can be detected (e.g., by a collection fiber and spectrometer). As shown, a multi-mode fiber can be placed near the capillary edge to collect the lasing emission with the other end sent to a spectrometer for analysis.

Demonstration of FRET lasing via a DNA scaffold can be accomplished using complementary ssDNA labeled with donor (i.e., Cy3) and acceptor (i.e., Cy5), respectively. After hybridization, when pumped with OPO laser at a wavelength in the donor absorption band, lasing emission can be seen from the acceptor emission wavelength range instead of the donor emission wavelength range. Since the acceptor is not directly excited by the pump laser, lasing emission from the acceptor results from energy transfer from the acceptor. Both the FRET lasing spectrum and lasing threshold can be determined. It should be noted that to avoid direct excitation of the acceptor, the pump laser can be tuned far away from the acceptor band while keeping enough spectral overlap with the donor absorption band.

In order to utilize the FRET microlaser for bio/chemical applications, it can be important in some instances to employ the lowest possible dye concentrations that support the lasing emission. Labeled ssDNA samples can be prepared at different concentrations, starting with 200 μM, where the concentration is then decreased until no lasing emission can be obtained. Due to the high Q-factor of the OFRR, a cut-off concentration in the sub-micromolar to several nanomolar range can be expected. In various aspects In various aspects, the energy transfer may be fluorescence resonance energy transfer (FRET), a molecular-beacon, or cavity-assisted radiative energy transfer. Besides non-radiative FRET, there is another energy transfer mechanism in an optical cavity called cavity-assisted radiative energy transfer, in which the emission from the donor is first coupled into the cavity, which stores photons for an extended amount of time before they are re-absorbed by the acceptor. The cavity-assisted transfer efficiency is determined by the fraction of donor emission into cavity modes and the probability of acceptor re-absorption. Since the cavity-assisted energy transfer does not require that the donor and acceptor be in close proximity, it generates a non-specific signal, which may deteriorate the sensing performance. Fortunately, the cavity-assisted energy transfer efficiency drops rapidly when the donor and acceptor concentration is below 10 μM, as shown in FIG. 19. Therefore, the FRET signal dominates in the range of interest.

Various DNA scaffolds can be used to control the FRET process and demonstrate how the FRET process affects the lasing properties. For example, such scaffolds can be used for DNA probe design for DNA detection and the DNA scaffold can be used to change the donor to acceptor ratio. As illustrated in FIGS. 20A-20C, the donor 120 to acceptor 122 ratio can be doubled from 1:1 to 2:1 using scaffold one-donor-one-acceptor (1D1A, FIG. 20A) and two-donor-one-acceptor (2D1A, FIG. 20B) while keeping the donor to acceptor distance unchanged. A scaffold similar to 2D1A scaffold may be used to determine cascade FRET lasing by using three dyes, including the donor 120, the acceptor 122, and a third dye 122A (see FIG. 20C).

In some aspects, the OFRR-FRET microlasers can be applied for ultrasensitive intracavity DNA detection. In various aspects, detection is based on colorimetric FRET. Upon the target analyte binding, the initial donor lasing emission will decrease. This type of detection is also called FRET turn-off detection. In various aspects, detection is based on the target analyte induced molecular beacon FRET lasing (or FRET turn-on detection). Under the present technology, detection limit can be established for these two schemes, respectively, and compared with existing FRET sensors carried out in a cuvette. Finally, single-base mismatch detection can be performed with perfect matched sequences, single nucleotide polymorphism (SNP) sequences, and a pool of random sequences, in order to demonstrate the selectivity of the FRET sensor.

FRET Turn-Off Sensor

As a non-limiting example, the principle of FRET turn-off sensor is illustrated in FIG. 21A-21B. The donor labeled probe ssDNA 130 can be first flowed through the OFRR capillary and the donor lasing can be achieved under pump laser excitation (see FIG. 21A). When acceptor labeled target ssDNA is present, it will hybridize with the probe ssDNA 132 and thus there is FRET between the donor and acceptor. In this case, the energy can be transferred efficiently to the target ssDNA, resulting in the cessation or significant decrease of the probe-ssDNA lasing emission (see FIG. 21B). In order to achieve the best quenching sensitivity, the OFRR/FRET laser sensor can be operated near the lasing threshold, where any small increase in the cavity loss (i.e., energy transfer to the target ssDNA in this case) will induce drastic decrease in the donor lasing emission. In addition, lasing emission from the acceptor can be monitored. Either a decrease in the donor laser emission or an increase in the acceptor laser emission can be used as the sensing transduction signal. The detection limit associated with each of these two sensing transduction signals can be compared.

For example, based on the present technology a 10 base pair (bp) probe-ssDNA may be used to establish sensing protocols and explore the detection limit for the target analyte. Then, different lengths of the probe-ssDNA samples (e.g., from 10 bp to 30 bp) can be tested. Since the quenching efficiency depends on the FRET efficiency between the dye pair labeled on the probe-ssDNA and target-ssDNA, respectively, there is a target sequence length limit for the FRET turn-off sensor. Accordingly, it can be determined how the detection limit decreases with the target sequence length. Finally, in order to overcome the length limit, an organic quencher, a gold nanoparticle, and a fluorescent conjugated polymer, all of which have a better quenching efficiency, can be used to replace the dye acceptor on the target analyte to compare the sensing performance with that obtained with regular dye acceptor. To demonstrate the sensor specificity, samples can be prepared by mixing perfect matched sequences, single-nucleotide polymorphism (SNP) sequences, and a pool of random sequences, and repeating these experiments.

MB FRET Turn-on Sensor

As a non-limiting example, the principle of MB FRET turn-on sensor is illustrated in FIGS. 27A-27B. MB works as the probe sequence labeled with dye and quencher. At its initial form, MB forms the stem-loop structure 134 with donor and quencher in the close proximity, and thus the emission from the donor is quenched (see FIG. 22A). When the target sequence is present, the hybridization of the target sequence with MB loop sequence 136 will open the MB and forms a linear structure, causing dye and quencher to be far apart. In the OFRR, the fluorescence from the donor will be amplified to achieve lasing emission (see FIG. 22B).

For example, the stem sequence in the MB can be varied. The kinetic strength of the stem sequence should be strong enough to maintain the stem-loop conformation within a small range of temperature fluctuation, but not too strong to prevent the MB to open upon hybridization with the complementary target sequence. Second, the detection protocol and the detection limit may be determined by using a 10 bp loop sequence MB probe, for example. The MB FRET turn-on sensor does not have sequence limit in terms of energy transfer; however, hybridization of longer sequence can cost longer time. A sequence length of 10-40 bp can be used to determine the sequence limitation based on detection limit and hybridization time. Third, samples can be prepared by mixing perfect matched sequences, single-nucleotide polymorphism (SNP) sequences, and a pool of random sequences to demonstrate the sensor specificity.

Example 2

In the following example, a sample contains SYTO 13® green fluorescent nucleic acid strain (Invitrogen) as the saturation dye and 21-bp ssDNA sequences. In this example, the sequences of the probe, the target, and the SNP are 5'-ACA ACA AAG ACA ATA CAT AGG-3' (SEQ ID NO:1), 5'-TGT TGT TTC TGT TAT GTA TCC-3' (SEQ ID NO:2), and 5'-TGT TGT TTC TAT TAT GTA TCC-3' (SEQ ID NO:3), respectively, and the ssDNAs are dissolved in buffer solution (tris acetate-EDTA, pH=8.3, Sigma-Aldrich) separately. The saturation dye, originally 5 mM solution in dimethyl sulfoxide, is mixed to the probe solution. Then the target solution is added to the sample, while the target is replaced with the SNP in another. A final concentration of both the DNAs and the saturation dye is 150 μm. Each solution is heated up to 50° C. and cooled down to room temperature to get rid of non-specific bindings in DNA sequences. As illustrated in FIG. 23A, the saturation dye does not have strong fluorescence by itself when there is only ssDNA. The saturation dye specifically binds to the dsDNA and emits light strongly; thus the sample has bright fluorescence only when the ssDNA probe is hybridized with the complementary ssDNA target as in FIG. 23B. FIG. 23C shows a schematic of the downstream optofluidic ring resonator (OFRR) laser system consisting of a thin-walled fused silica microcapillary. The system is uniformly pumped by a 5 ns pulsed optical parametric oscillator (OPO) at 488 nm, and the light confined by the whispering gallery mode (WGM) evanescently interacts with the sample solution flowing inside the OFRR. The lasing emission is picked up by a spectrometer (Horiba iHR550) through the free space coupling. The diameter and the wall thickness of the OFRR are 80 μm and 5 μm, respectively.

The lasing signal from the target and the SNP is presented in FIGS. 24A-24B. The detailed study using a higher spectral resolution shows a typical multi-mode lasing (see FIG. 24A) around 548 nm, which indicates the saturation dye, along with the dsDNA, is able to achieve the lasing emission. As compared to the target lasing, the SNP shows very low lasing signal, since the SNP has a lower fraction of the hybridization with the probe than the target. FIG. 24B illustrates the laser intensity as a function of pump energy density. The target laser has a lasing threshold of 305 μJ/mm2 and fairly high lasing efficiency, while the SNP laser shows very low lasing intensity even with the high pump energy density. At the energy density of 1.1 mJ/mm2, the target signal shows about 21.4 times higher signal intensity than the SNP, which is considerably higher ratio than that of many fluorescence-based DNA detection techniques.

In this example lasing is achieved from the saturation dye and the DNA mixture, which can be utilized to differentiate the target DNA and the SNP. The target and the SNP show distinguishable lasing characteristics, thus enabling rapid and selective detection of the SNP. The detection method does not require complexity such as labeling, and is a competitive technology in mutation scanning for medical diagnosis and biological researches.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A method of detecting a target analyte, the method comprising:
binding the target analyte and a probe comprising at least one fluorophore to form a fluid composition;
exciting the fluid composition within a laser cavity; and
measuring a laser emission from the fluid composition based on an interaction between the target analyte and the probe.

2. The method of claim 1, further comprising hybridizing the target analyte and the probe, prior to the exciting.

3. The method of claim 2, wherein the fluorophore is a saturation dye, an acceptor fluorophore, a donor fluorophore or a fluorescent protein.

4. The method of claim 1, wherein the laser cavity is an optofluidic ring resonator (OFRR) microlaser with an intracavity biosensing platform.

5. The method of claim 1, wherein the interaction is selected from the group consisting of an energy transfer, intercalation, hybridization of the target analyte and the probe, and combinations thereof.

6. The method of claim 5, wherein the energy transfer occurs when an acceptor fluorophore and a donor fluorophore are separated by a distance of greater than or equal to about 1 nm to less than or equal to about 20 nm when the target analyte hybridizes with the probe.

7. The method of claim 5, wherein the energy transfer comprises one of fluorescence resonance energy transfer (FRET), or fluorescence resonance energy transfer (FRET) with a molecular-beacon.

8. The method of claim 1, wherein the target analyte is selected from the group consisting of a protein, an enzyme, a receptor, an antibody fragment, a peptide, a carbohydrate, nucleic acids, single-stranded DNA, double-stranded DNA, RNA, an oligonucleotide, a single-nucleotide polymorphism (SNP) sequence, and any combination thereof.

9. The method of claim 1, further comprising exposing the target analyte to an activity, wherein the activity causes a detectable change in the target analyte.

10. The method of claim 9, wherein the detectable change is one of binding, dissociation, enzymatic cleavage, or a conformational change.

11. A method of detecting a DNA molecule, the method comprising:
labeling the DNA molecule with an acceptor fluorophore;
labeling at least one probe with a donor fluorophore;
hybridizing the DNA molecule and the probe to create a fluid composition, wherein upon hybridization the acceptor fluorophore and the donor fluorophore are separated by greater than or equal to about 1 nm to less than or equal to about 20 nm;
exciting the fluid composition within a laser cavity;
transferring energy between the donor fluorophore and the acceptor fluorophore by fluorescence resonance energy transfer (FRET) to generate a laser emission from the fluid composition and the laser cavity; and
measuring the laser emission to thereby detect the DNA molecule.

12. A method of detecting a DNA molecule, the method comprising:
combining a single-stranded DNA molecule and a single-stranded probe with a saturation dye to form a fluid composition;
exciting the fluid composition within a laser cavity; and
measuring a laser emission from the fluid composition based on an interaction between the single-stranded DNA molecule and the single-stranded probe.

13. A method of detecting a target analyte, the method comprising:
binding the target analyte and a probe comprising a gain medium to form a fluid composition;
exciting the fluid composition within a laser cavity; and
measuring a laser emission from the fluid composition based on an interaction between the target analyte and the probe.

14. The method of claim 13, wherein the gain medium comprises a fluorophore or a dye.

15. The method of claim 13, wherein exciting the fluid composition within a laser cavity comprises exciting the fluid composition within a laser cavity that is a cross-section of a capillary that forms a ring resonator that supports a whispering gallery mode (WGM).

16. The method of claim 15, wherein the WGM has a Q-factor great than $10^7$.

17. The method of claim 15, wherein the capillary comprises capillary walls with a thickness of less than or equal to about 10 µm.

18. The method of claim 15, wherein exciting the fluid composition further comprises interacting the WGM with the gain medium to generate the laser emission.

19. The method of claim 13, wherein measuring a laser emission from the fluid composition comprises measuring a laser emission from the fluid composition through free space with a detector.

20. The method of claim 13, wherein measuring a laser emission from the fluid composition comprises contacting an optical fiber, a fiber prism or a waveguide to the laser cavity and measuring the laser emission through the optical fiber, fiber prism or waveguide with a detector.

* * * * *